United States Patent [19]
Fisher et al.

[11] Patent Number: 6,117,413
[45] Date of Patent: *Sep. 12, 2000

[54] RADIONUCLIDE-BINDING COMPOUND, A RADIONUCLIDE DELIVERY SYSTEM, A METHOD OF MAKING A RADIUM COMPLEXING COMPOUND, A METHOD OF EXTRACTING A RADIONUCLIDE, AND A METHOD OF DELIVERING A RADIONUCLIDE

[75] Inventors: Darrell R. Fisher, Richland, Wash.; Chien M. Wai; Xiaoyuan Chen, both of Moscow, Id.

[73] Assignees: Battelle Memorial Institute, Richland, Wash.; Idaho Research Foundation, Inc., Moscow, Id.

[*] Notice: This patent is subject to a terminal disclaimer.

[21] Appl. No.: 08/968,022

[22] Filed: Nov. 12, 1997

[51] Int. Cl.$^7$ .............. A61K 51/00; A61M 36/14

[52] U.S. Cl. .............. 424/1.37; 424/1.65; 424/1.11; 424/1.49; 424/1.81; 424/1.69; 534/10; 549/347

[58] Field of Search .............. 424/1.37, 1.11, 424/1.49, 1.65, 1.69, 9.1, 1.81; 534/7, 10–16; 549/347, 348, 352, 350, 349

[56] References Cited

U.S. PATENT DOCUMENTS

| | | | |
|---|---|---|---|
| 5,116,614 | 5/1992 | Ehrenfeld | 434/92 |
| 5,246,691 | 9/1993 | Geerlings et al. | 424/1.1 |

FOREIGN PATENT DOCUMENTS

| | | | |
|---|---|---|---|
| 07206825 | 8/1995 | Japan | C07D 323/00 |
| 94/24138 | 10/1994 | WIPO | 493/8 |
| 95/01346 | 1/1995 | WIPO | 257/2 |
| 96/14878 | 5/1996 | WIPO | 49/50 |
| 97/33628 | 9/1997 | WIPO | 51/12 |

OTHER PUBLICATIONS

"Synthesis and Properties of Calixcrown Telomers", by Zhen–Lin Zhong, Chun–Ping Tang, Cai–Ying Wu, and Yuan–Yin Chen. p. 1737. 1995.

"Crown Ether Derivatives of Calix[5]arenes: Synthesis and Complexation Properties", by Francoise Arnaud–Neu, Ralf Arnecke, Volker Bohmer, Stefano Fanni, James L.M. Gordon, Marie–Jose Schwing–Weill and Walter Vogt. p. 1855–1860. 1996.

"Selective Lower Rim Reactions of 5,17–Upper Rim–Disubstituted Calix[4]arenes", by Shiv Kumar Sharma and C. David Gutsche. p. 2654–2568. 1995.

The Feasibility of $^{255}$ac as a source of a–particles in radioimmunotherapy, M.W. Geerlings, et al., Nuclear Medicine Communiations (1993) 14, 121–125.

Potential Use of Alpha Emitting Radionuclides in the Treatment of Cancer, D.S. Wilbur, Antibody, Immunoconjugates and Radiopharmaceuticals, vol. 4, No.1, 1991.

Radionuclides for radioimmunotherapy: criteria for selection, M.W. Geerlings, The International Journal of Biological Markers/ vol. 8 No. 3, pp. 180–186.

Selectivity of Calix[4]arene–crown–6 for Cesium Ion in ISE: Effect of the Conformation, C Bocchi et al., Dipartimento di Chimica, Analytical Chemistry, vol. 87, No. 23, 1995.

Blixt et al J. Am. Chem. Soc., 1995, 117, 8536–8540, "Kinetics and Mechanism of the Sodium Cation complexation by 5,11,17,23–tetra–p–tert–butyl–25,26,27,28–tetramethoxy–calix[4]arene in solution."

Chang, J. Chem. Soc. Perkin Trans. I, 1986, 2, 211–14, "New Metal Cation–Selective Ionophores Derived from Calixarenes: Their Syntheses and Ion–Binding Properties".

Shortreed et al, Anal. Chem, 1996, 68, 2656–2662, "Minature Sodium Selective Ion Exchange Optode with Fluorescent $^P$H Chromoionophores and Tunable Dynamic Range".

Arduini et al, J. Chem. Soc. Chem. Commun., 1990, 22, 1597–8, Selective–1,2–Functionalization of Calix[4]arenes at the lower rim. Synthesis of a new type of bis–calixcrown ether.

Primary Examiner—Jose' G. Dees
Assistant Examiner—Dameron Jones
Attorney, Agent, or Firm—Wells, St. John, Roberts, Gregory & Matkin P.S.

[57] ABSTRACT

The invention pertains to compounds which specifically bind radionuclides, and to methods of making radionuclide complexing compounds. In one aspect, the invention includes a radionuclide delivery system comprising: a) a calix[n]arene-crown-[m]-ether compound, wherein n is an integer greater than 3, and wherein m is an integer greater than 3, the calix[n]arene-crown-[m]-ether compound comprising at least two ionizable groups; and b) an antibody attached to the calix[n]arene-crown-[m]-ether compound. In another aspect, the invention includes a method of making a radium complexing compound, comprising: a) providing a calix[n]arene compound, wherein n is an integer greater than 3, the calix[n]arene compound comprising n phenolic hydroxyl groups; b) providing a crown ether precursor, the crown ether precursor comprising a pair of tosylated ends; c) reacting the pair of tosylated ends with a pair of the phenolic hydroxyl groups to convert said pair of phenolic hydroxyl groups to ether linkages, the ether linkages connecting the crown ether precursor to the calix[n]arene to form a calix[n]arene-crown-[m]-ether compound, wherein m is an integer greater than 3; d) converting remaining phenolic hydroxyl groups to esters; e) converting the esters to acids, the acids being proximate a crown-[m]-ether portion of the calix[n]arene-crown-[m]-ether compound; and f) providing a $Ra^{2+}$ ion within the crown-[m]-ether portion of the calix[n]arene-crown-[m]-ether compound.

47 Claims, 31 Drawing Sheets

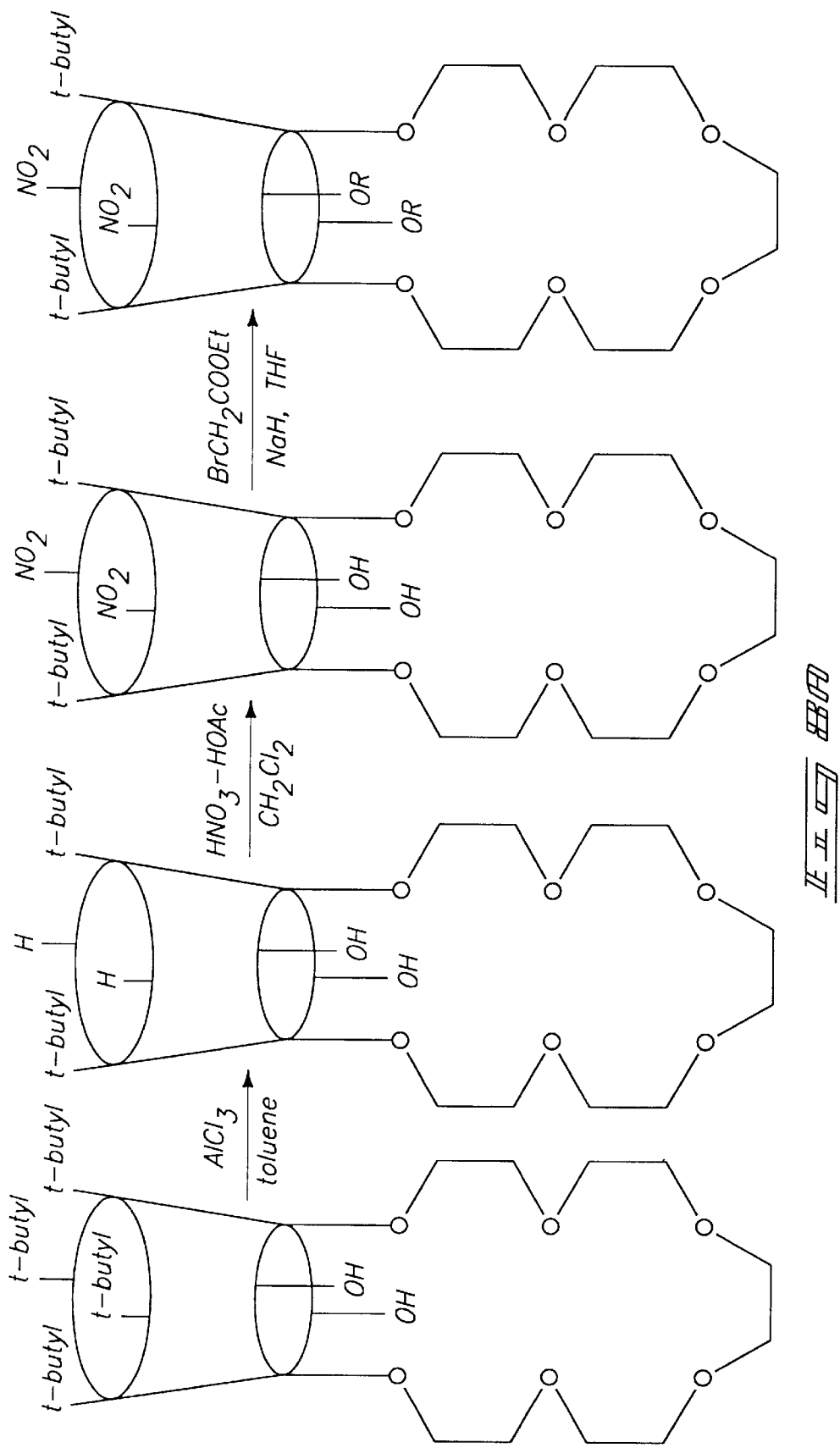

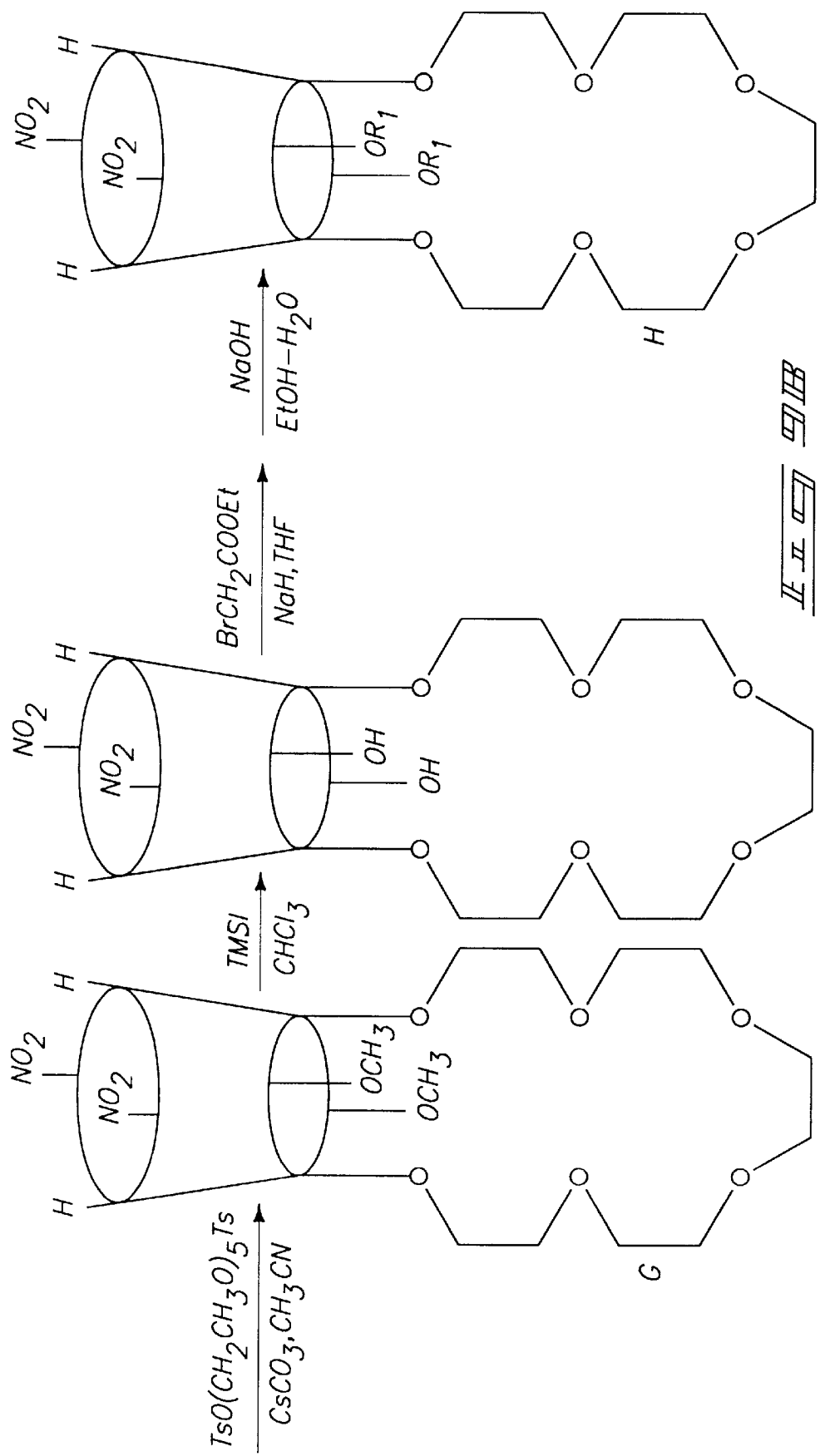

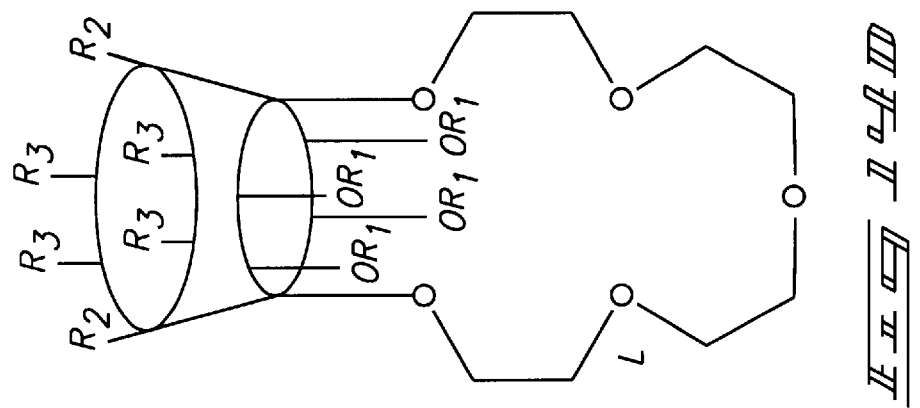
FIG. 14D
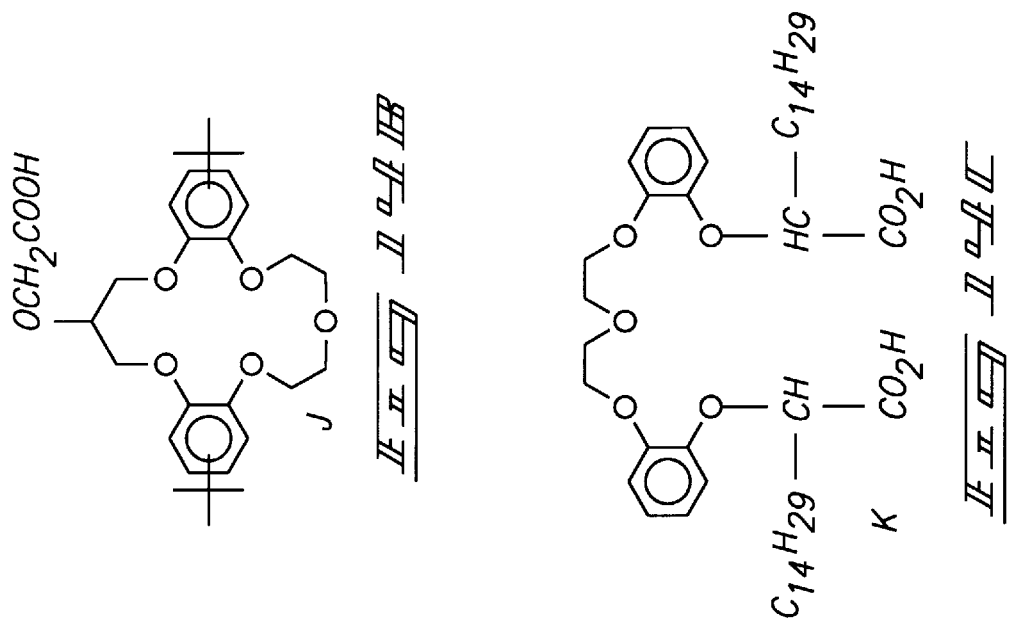
FIG. 14B
FIG. 14C
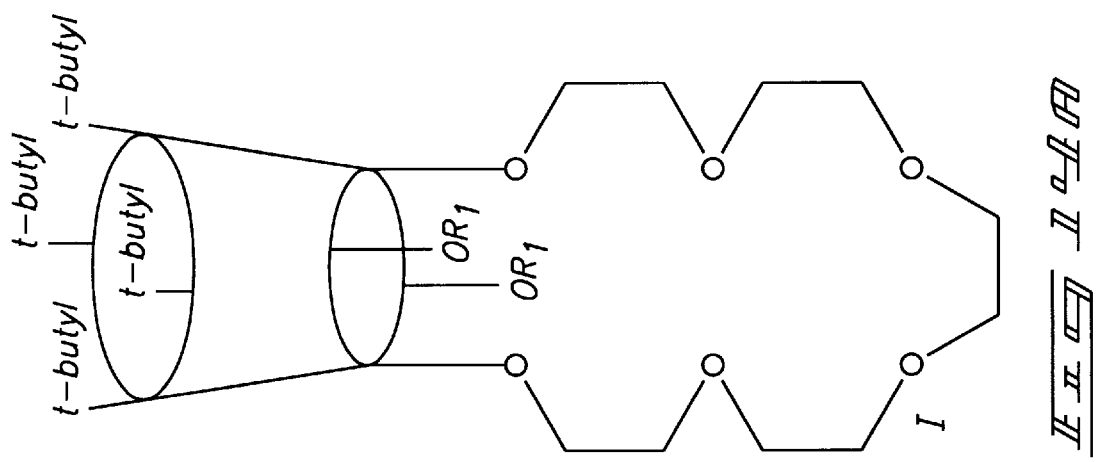
FIG. 14A

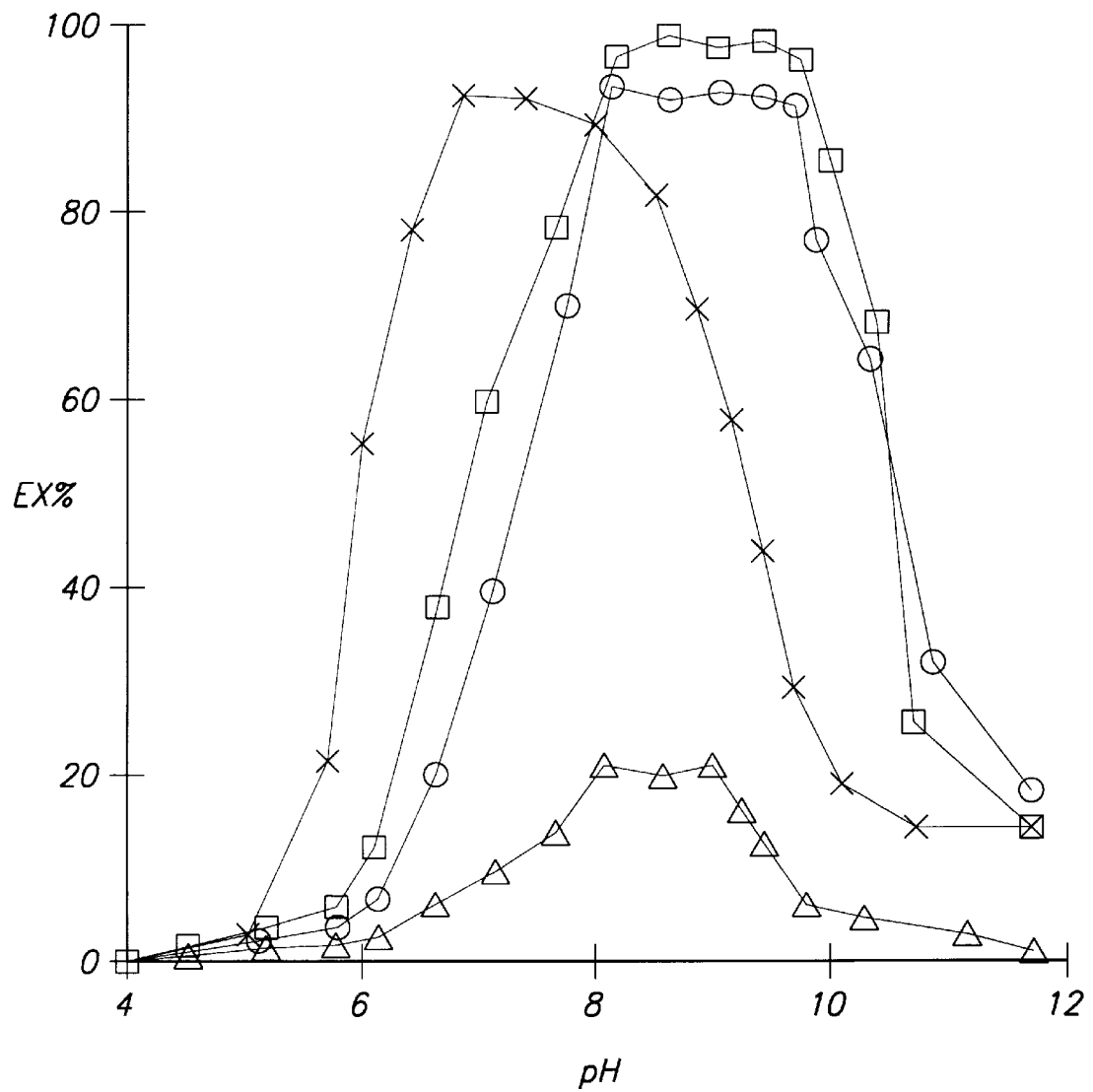

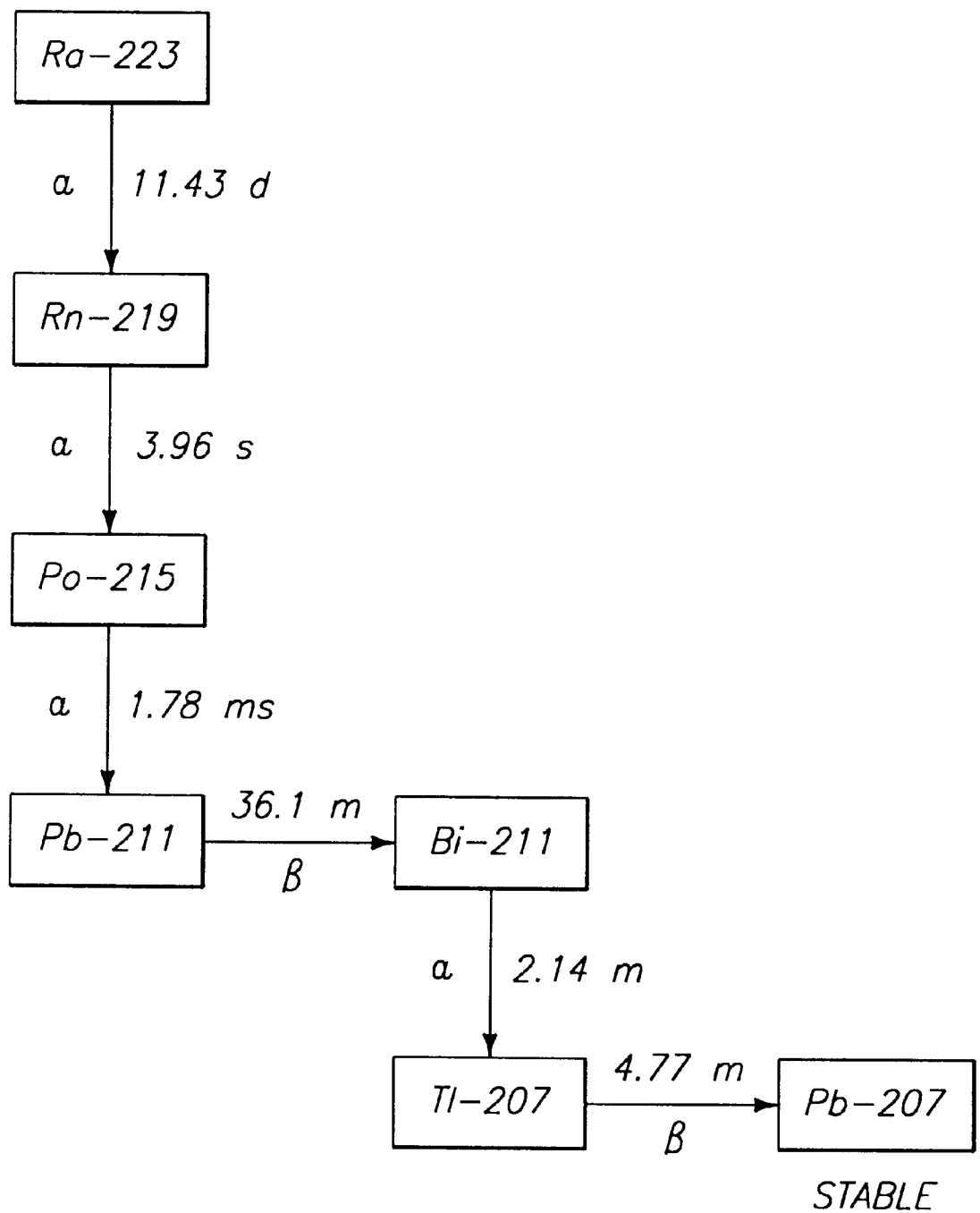

RADIONUCLIDE-BINDING COMPOUND, A RADIONUCLIDE DELIVERY SYSTEM, A METHOD OF MAKING A RADIUM COMPLEXING COMPOUND, A METHOD OF EXTRACTING A RADIONUCLIDE, AND A METHOD OF DELIVERING A RADIONUCLIDE

TECHNICAL FIELD

The invention pertains to compounds which specifically bind radionuclides, and to methods of making radionuclide complexing compounds. The invention further pertains to radionuclide delivery systems and to methods of utilizing radionuclide delivery systems. Additionally, the invention pertains to methods of extracting radionuclides.

BACKGROUND OF THE INVENTION

Radionuclides have many uses. For instance, in medicine radionuclides are frequently used to kill undesired cells, such as cancer cells. A difficulty in utilizing radionuclides for killing cancer cells is in localizing the radionuclides to the proximity of tumors and cancer cells while sparing normal cells and tissues. Radionuclides kill cells by emitting ionizing radiation. Cells will die when sufficient numbers of ionizing events take place within the cell nuclei. Accordingly, the radionuclides must be localized near cancer cells. The ionizing radiation then interacts with cell nuclei such that cancer cells are more likely to be killed than non-cancerous cells.

Radionuclides are also used in science as tracers and in nuclear power generation processes. The use of radionuclides leads to waste products contaminated with radioactive components. Such waste products are difficult to dispose of safely. If the radionuclides could be selectively removed from the waste product, the remaining material of the waste product could be disposed of by conventional means.

It would be desirable to develop methods for localizing radionuclides near cells which are to be selectively killed. It would also be desirable to develop methods for selectively separating waste radionuclides from non-radioactive waste constituents.

BRIEF DESCRIPTION OF THE DRAWINGS

Preferred embodiments of the invention are described below with reference to the following accompanying drawings.

FIGS. 3A–C illustrate formulaic representations of calix[n]arene-crown-[m]-ether compounds of the present invention.

FIGS. 4A–L illustrate formulaic representations of calix[n]arene-crown-[m]-ether compounds of the present invention.

FIGS. 5A–I illustrate formulaic representations of calix[n]arene-crown-[m]-ether compounds of the present invention.

FIG. 13 illustrates a process for attaching a methylchloride derivative to a calix[4]arene-crown-[6]-ether compound of the present invention.

FIGS. 14A–D illustrate four ether compounds for which the $Ra^{2+}$ selectivity is tabulated in Table I.

FIG. 15 is a graph of the $Ra^{2+}$ selectivity of the FIG. 13A–D compounds relative to pH.

FIG. 16 is a decay profile of Ra-223.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In one aspect, the invention encompasses a radionuclide delivery system comprising:
   a calix[n]arene-crown-[m]-ether compound, wherein n is an integer greater than 3, and wherein m is an integer greater than 3, the calix[n]arene-crown-[m]-ether compound comprising at least two ionizable groups; and
   an antibody attached to the calix[n]arene-crown-[m]-ether compound.

In another aspect, the invention encompasses a compound comprising:
   a calix[n]arene group, wherein n is an integer greater than 3 and less than 7, the calix[n]arene group comprising an upper rim and a lower rim;
   at least two ionizable groups attached to the lower rim;
   a crown ether attached to the lower rim; and
   a $Ra^{2+}$ ion held within the crown ether.

In yet another aspect, the invention encompasses a method of making a radium complexing compound, comprising:
   providing a calix[n]arene compound, wherein n is an integer greater than 3, the calix[n]arene compound comprising n phenolic hydroxyl groups;
   providing a crown ether precursor, the crown ether precursor comprising a pair of tosylated ends;
   reacting the pair of tosylated ends with a pair of the phenolic hydroxyl groups to convert said pair of phenolic hydroxyl groups to ether linkages and to leave remaining unreacted phenolic hydroxyl groups, the ether linkages connecting the crown ether precursor to the calix[n]arene to form a calix[n]arene-crown-[m]-ether compound, wherein m is an integer greater than 3;
   converting at least some of the remaining phenolic hydroxyl groups to esters;

converting the esters to acids, the acids being proximate a crown-[m]-ether portion of the calix[n]arene-crown-[m]-ether compound; and providing a $Ra^{2+}$ ion within the crown-[m]-ether portion of the calix[n]arene-crown-[m]-ether compound.

Figure 1B:
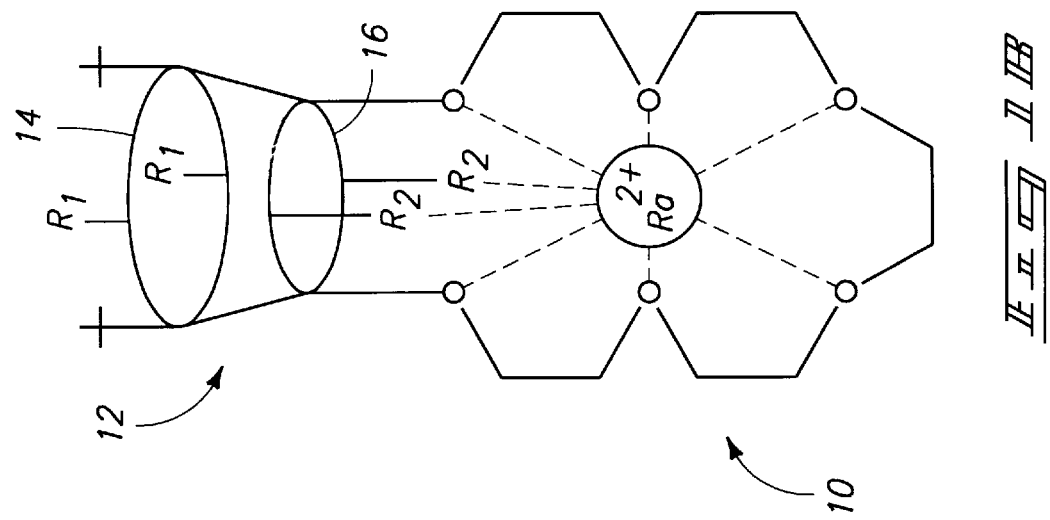
FIGS. 1A and B illustrate two formulaic representations of a t-butyl-calix[4]arene-crown-[6]-ether of the present invention.
Figure 1A:
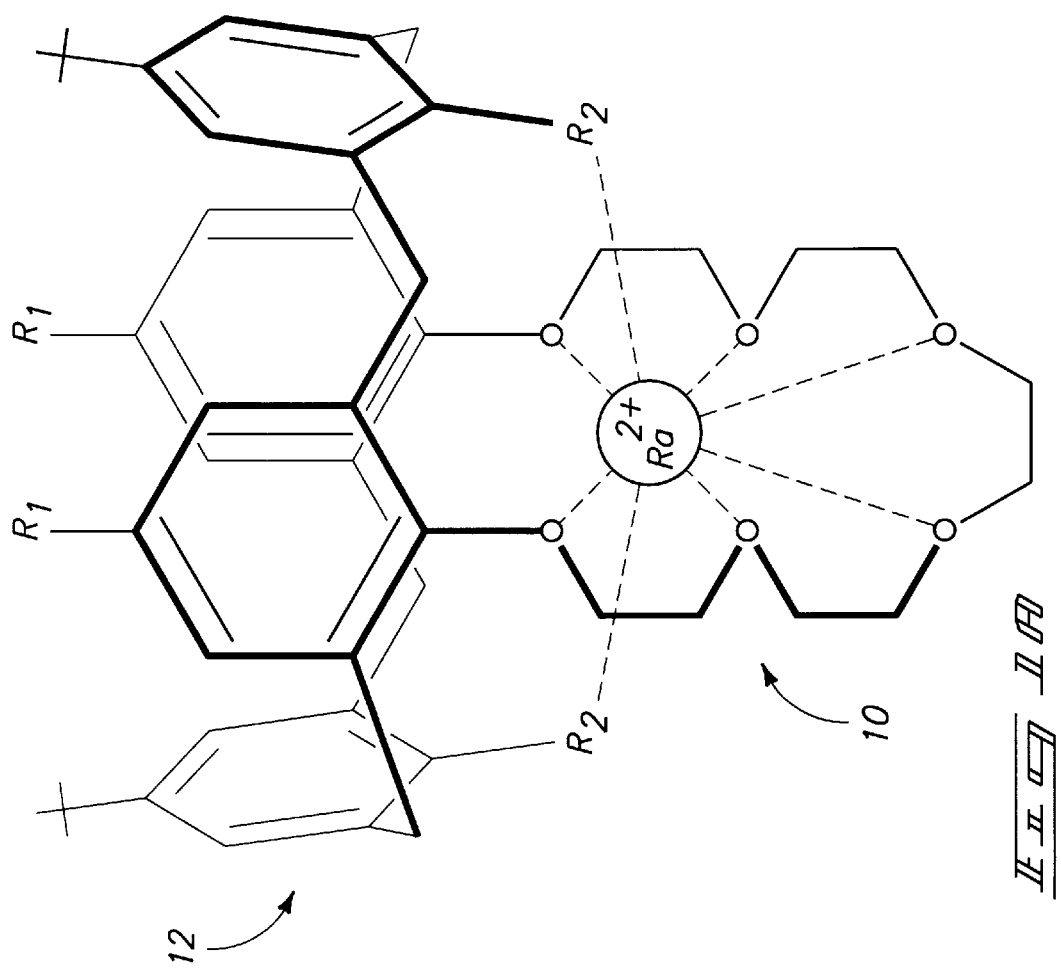

More specifically, the invention encompasses compounds which selectively bind particular radionuclides, and which bind such radionuclides tightly. Referring to FIGS. 1A and B, a compound of the present invention is illustrated in two alternative formulaic representations. The illustrated compound is t-butyl-calix[4]arene-crown-[6]-ether dicarboxylic acid, which has been found to selectively and tightly bind $Ra^{2+}$. FIG. 1A shows that the compound consists of a crown-[6]-ether portion 10 comprising six oxygens. A calix [4]arene portion 12 is attached to crown-[6]-ether portion 10 through two of the oxygens of crown-[6]-ether portion 10. The calix[4]arene compound comprises four aromatic rings joined in a cyclic arrangement. FIG. 1B shows that the cyclic arrangement of aromatic rings of calix[4]arene portion 12 can be represented as a cone. The cone comprises an upper rim 14 and a lower rim 16. Attached to upper rim 14 are two tertiary butyl groups and two functional groups represented as $R_1$. Groups $R_1$ can be configured for linking the t-butyl-calix[4]arene-crown-[6]-ether to a protein. Accordingly, groups $R_1$ can comprise linking groups having one or more functional groups selected from the group consisting of amines, aldehydes, esters, alcohols, azides, cyanides, halogens, anhydrides, and acid chlorides. For example, the groups labeled $R_1$ can comprise $NH_2$, I, $CH_2CHO$, $CH_2CH_2OH$, $CH_2CH_2Br$, $CH_2CH_2N_3$, $CH_2CH_2NH_2$, $CH_2CH_2CN$, CHO, $CH_2Cl$, $CH_2NO_2$, $CH_2CH(COOEt)_2$ and $CH_2OR$, wherein R represents an alkene.

Lower rim 16 is attached to crown-[6]-ether portion 10, and is further attached to a pair of ionizable groups labeled as $R_2$. The ionizable groups $R_2$ preferably comprise a negative charge when in an ionized form. Such ionizable groups can comprise, for example, one or more functional groups selected from the group consisting of carboxylic acid, hydroxamic acid, phosphonic acid, sulfonic acid, and diphosphonic acid.

The ionizable groups $R_2$ extend from opposing sides of lower rim 16 to bind to opposing sides of a radionuclide held within crown-[6]-ether portion 10. Accordingly, a radium ion held within crown-[6]-ether portion 10 comprises covalent-coordination bonds to the six oxygens of crown-[6]-ether portion 10 as well as to both ionizable groups $R_2$. The negative charges of ionizable groups $R_2$ neutralize the positive charges on the $Ra^{2+}$ ion.

Figure 2:
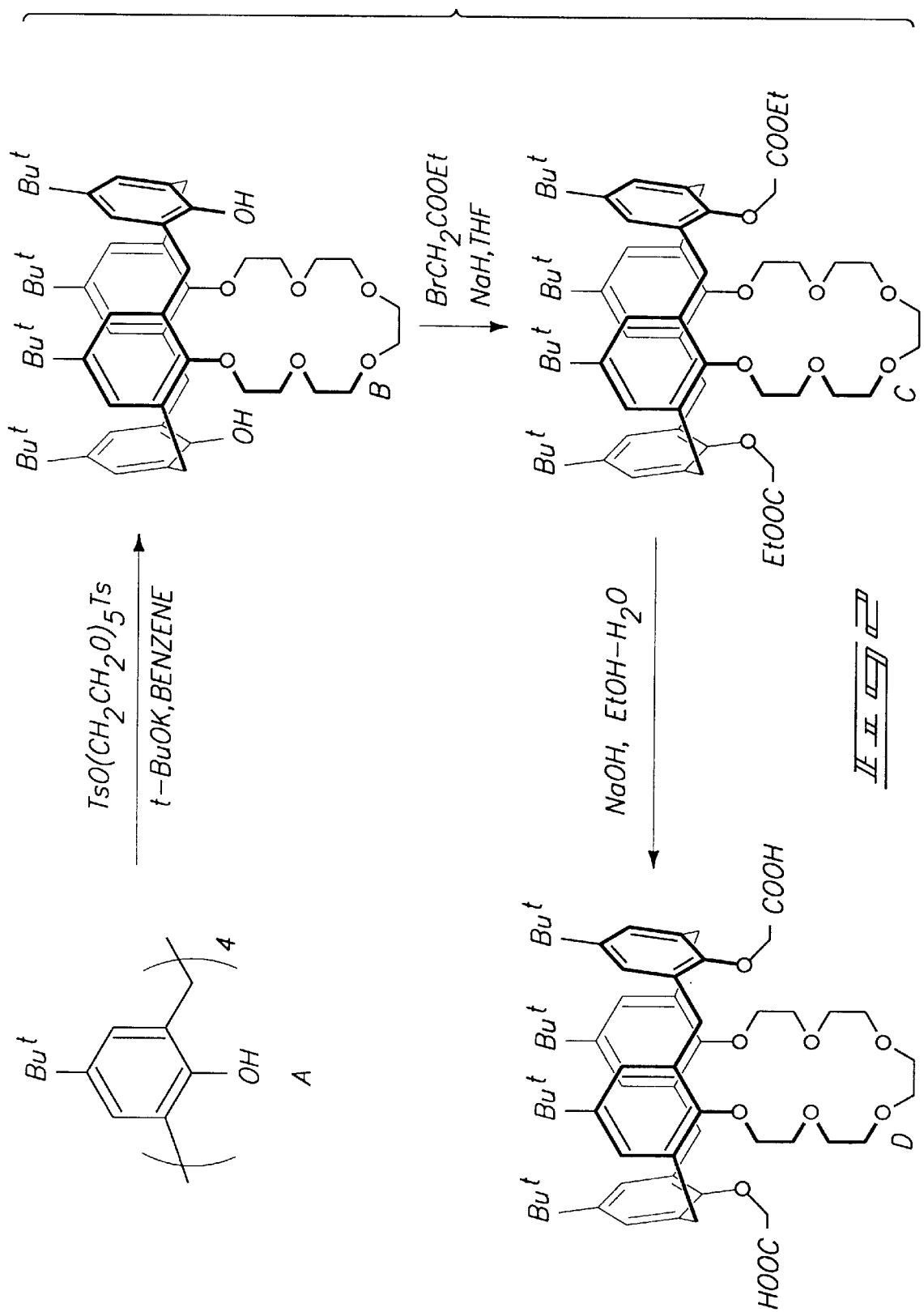
FIG. 2 is a diagrammatic view of a reaction process for forming a t-butyl-calix[4]arene-crown-[6]-ether compound.
Figures 4A, 4B:
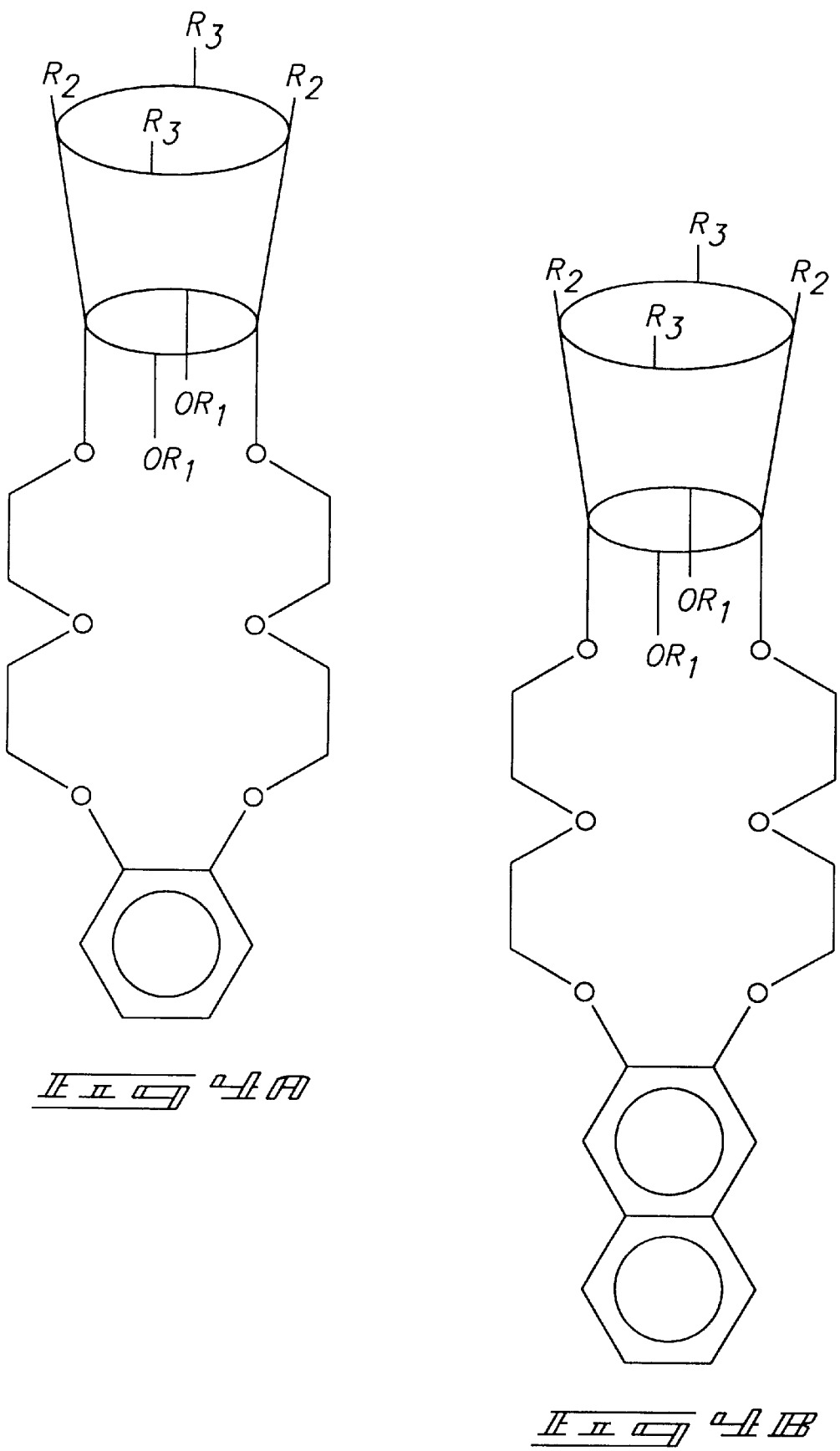
Figure 4D:
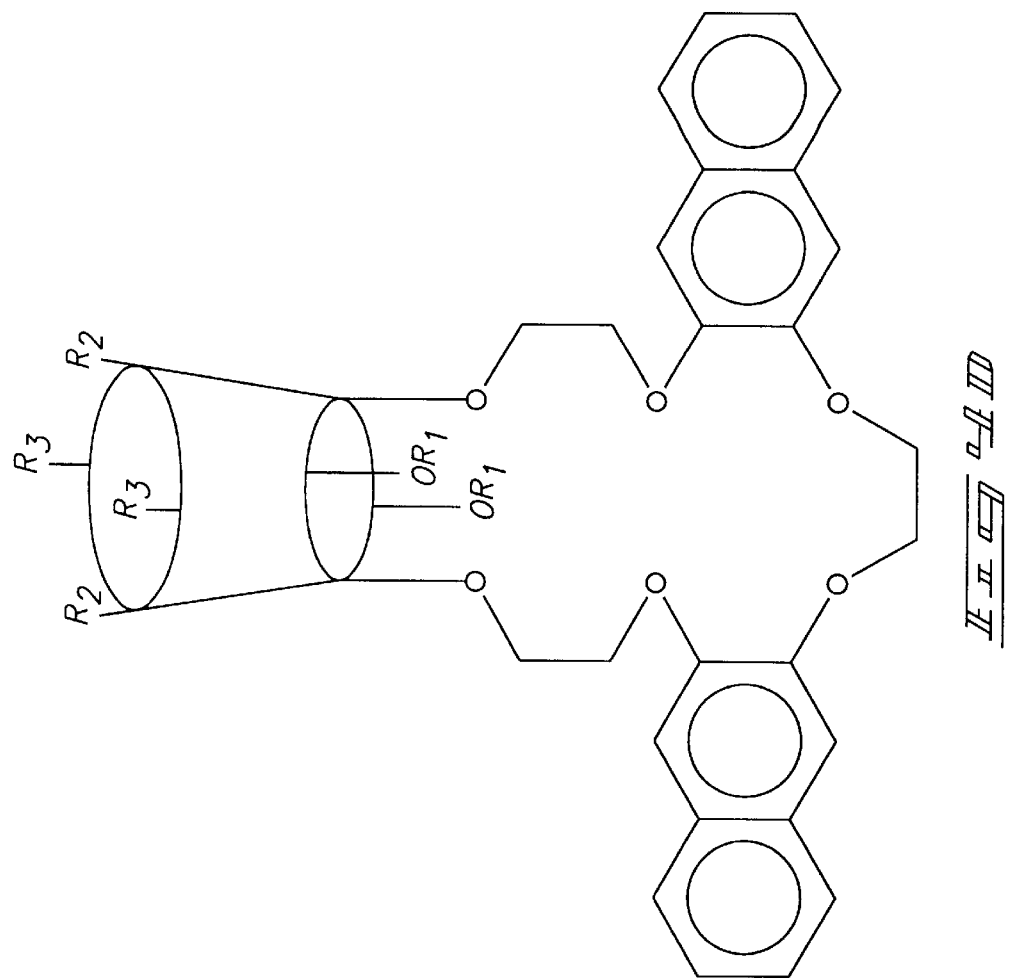
Figure 4C:
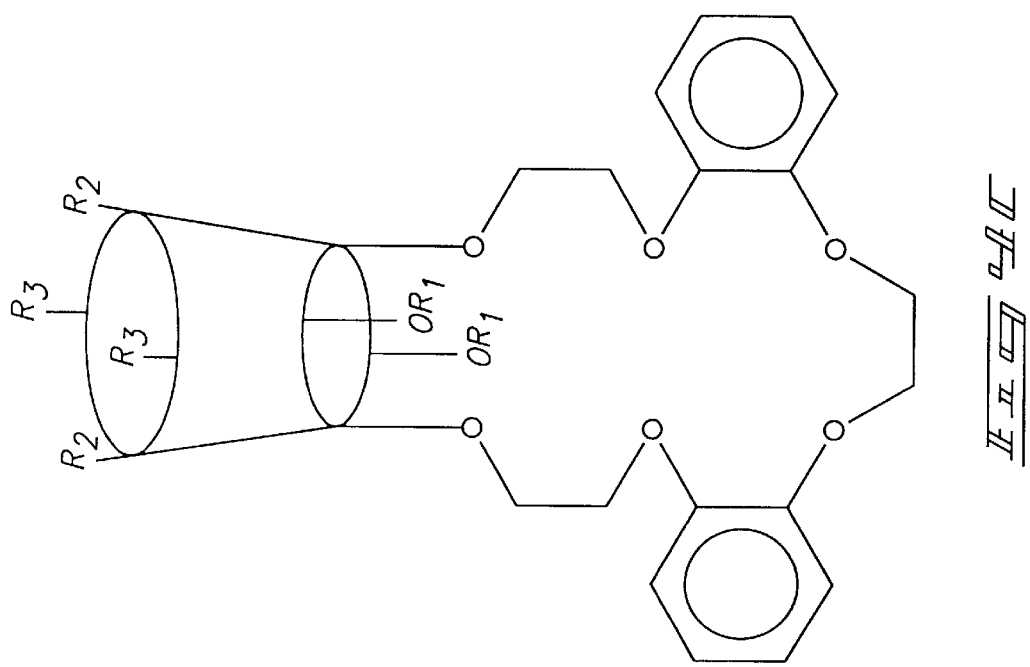
Figure 4F:
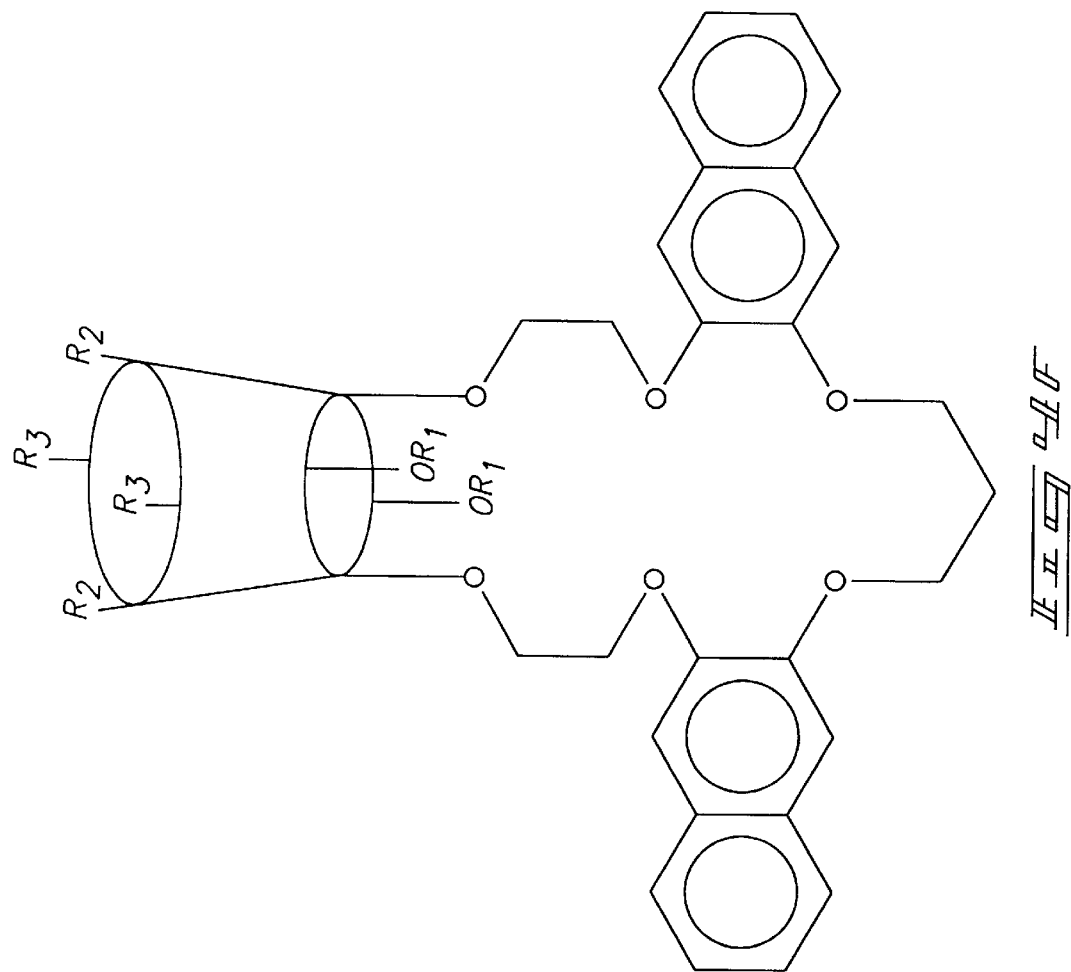
Figure 4E:
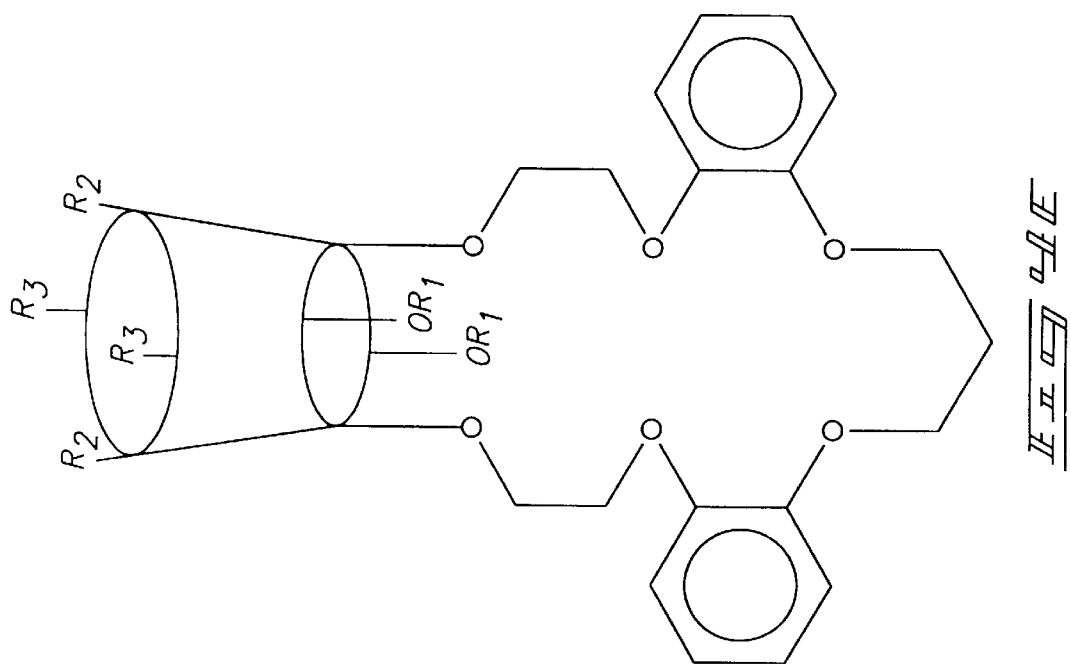
Figure 6H:
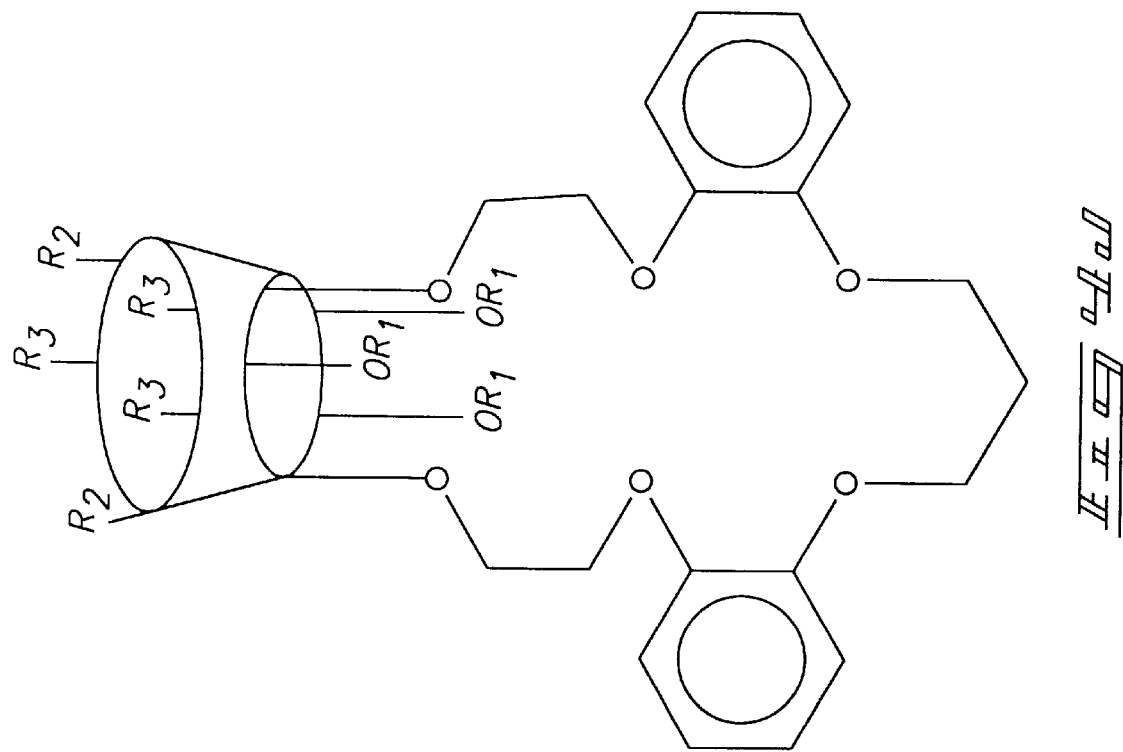
FIGS. 6A–C illustrate formulaic representations of calix[n]arene-crown-[m]-ether compounds of the present invention.
Figure 6I:
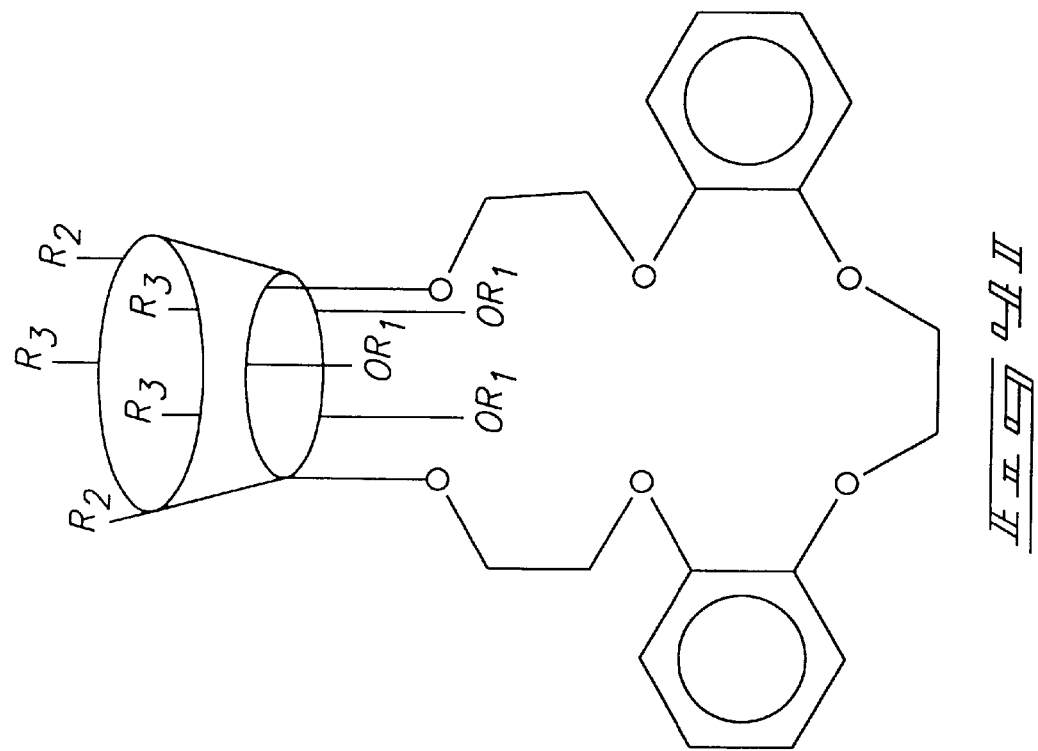
Figure 4L:
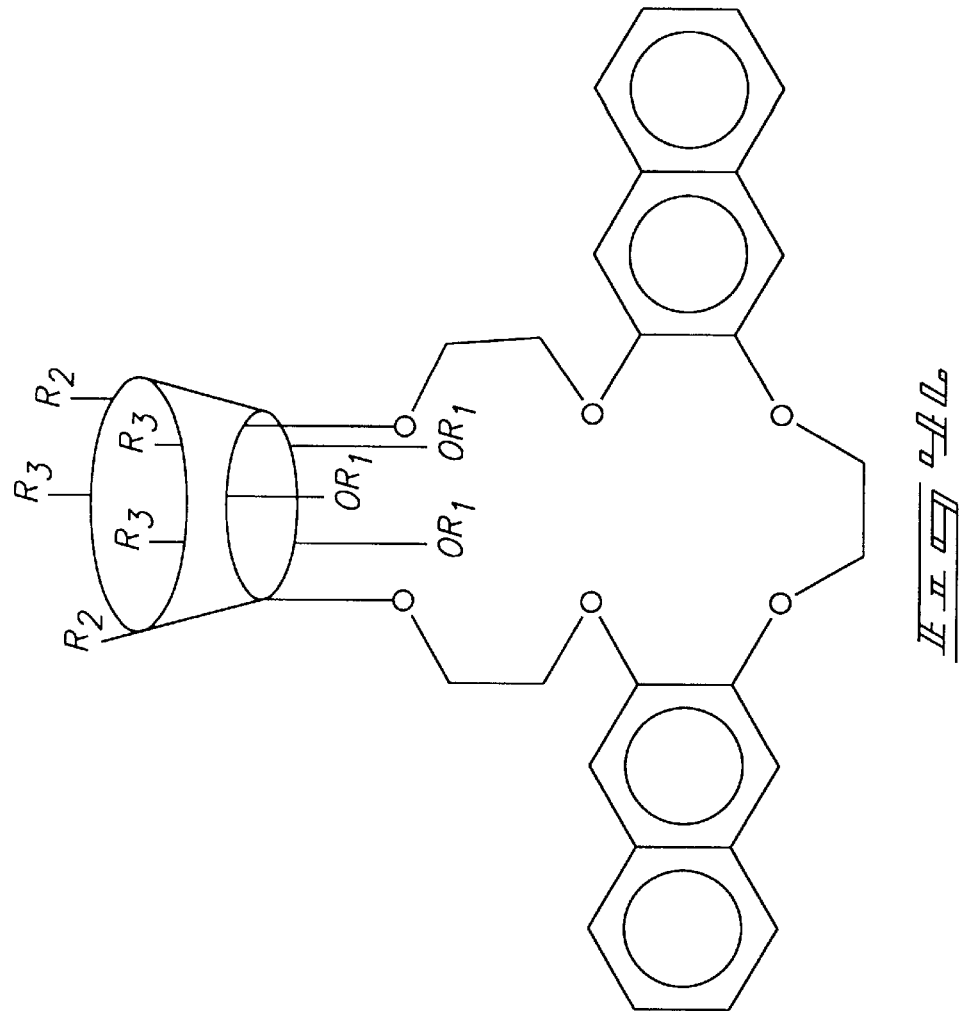
Figure 4K:
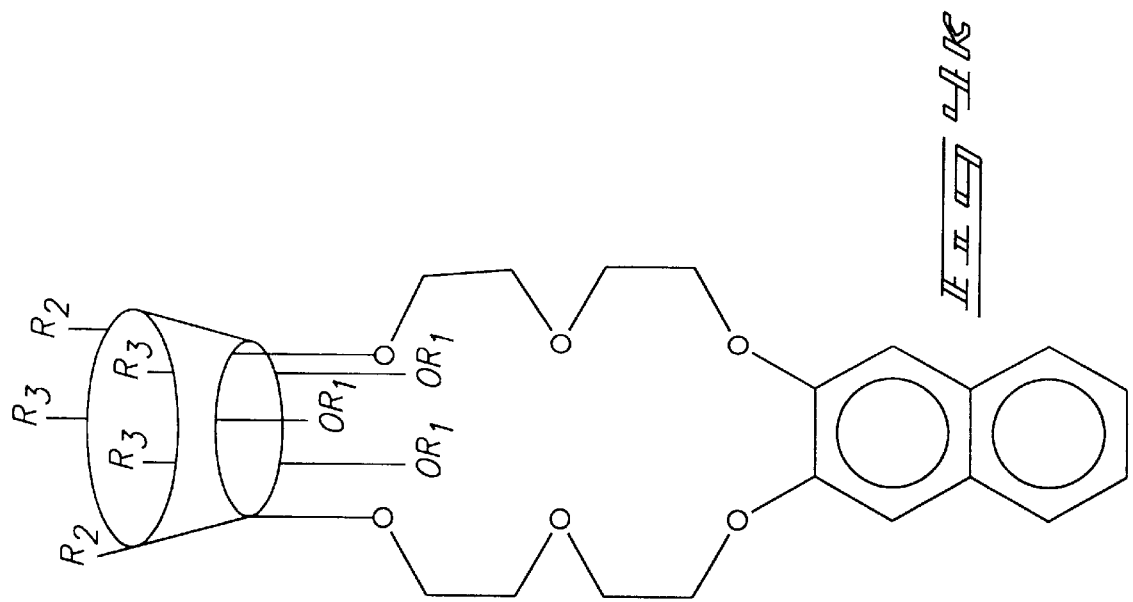
Figure 5B:
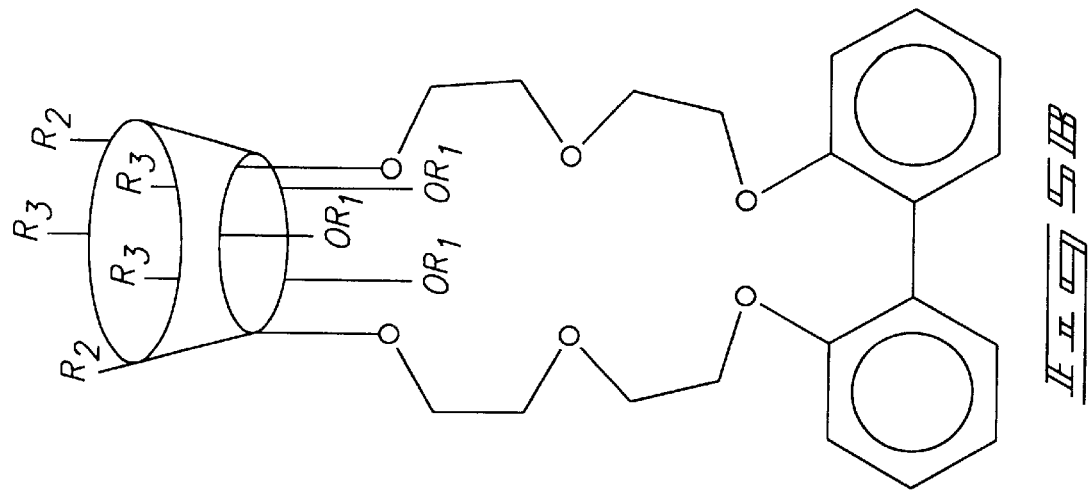
Figure 5A:
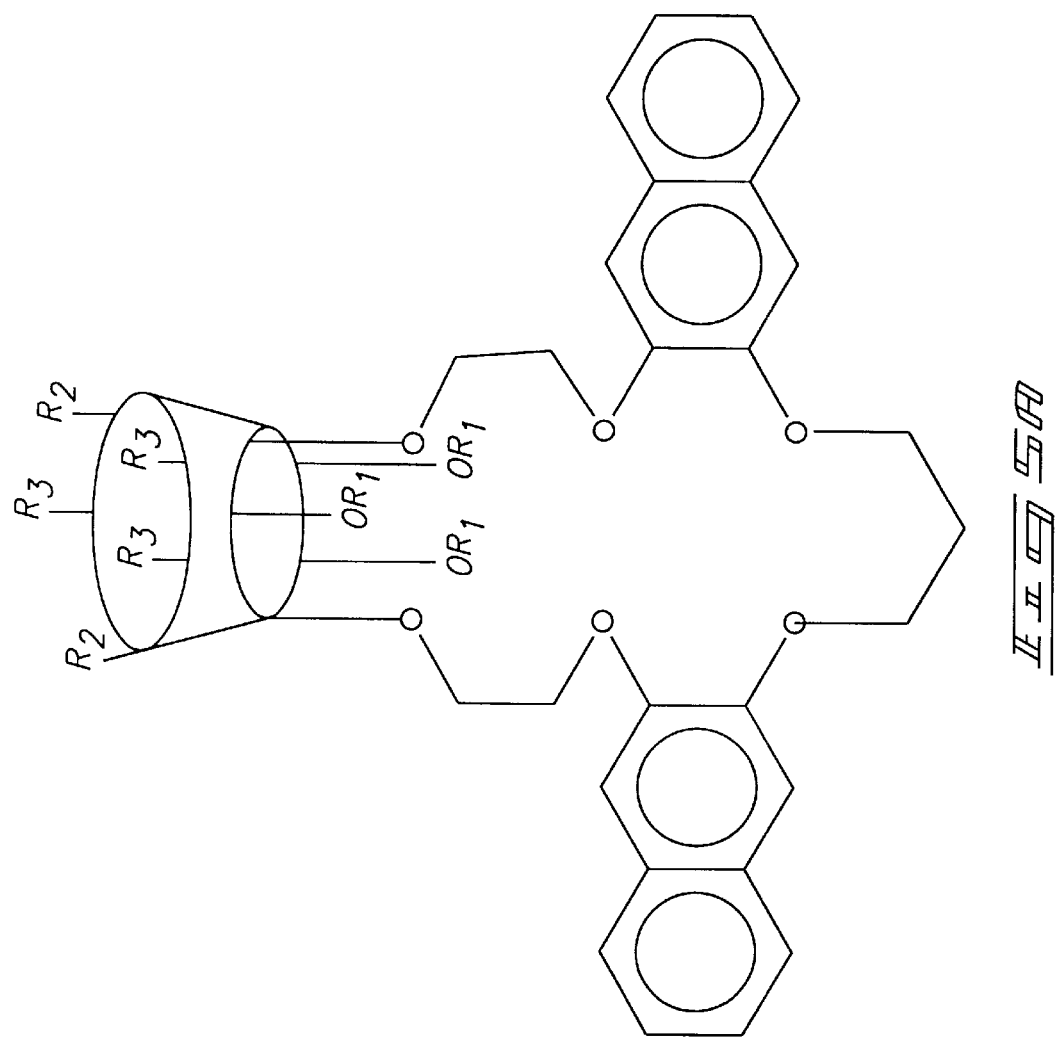
Figure 5D:
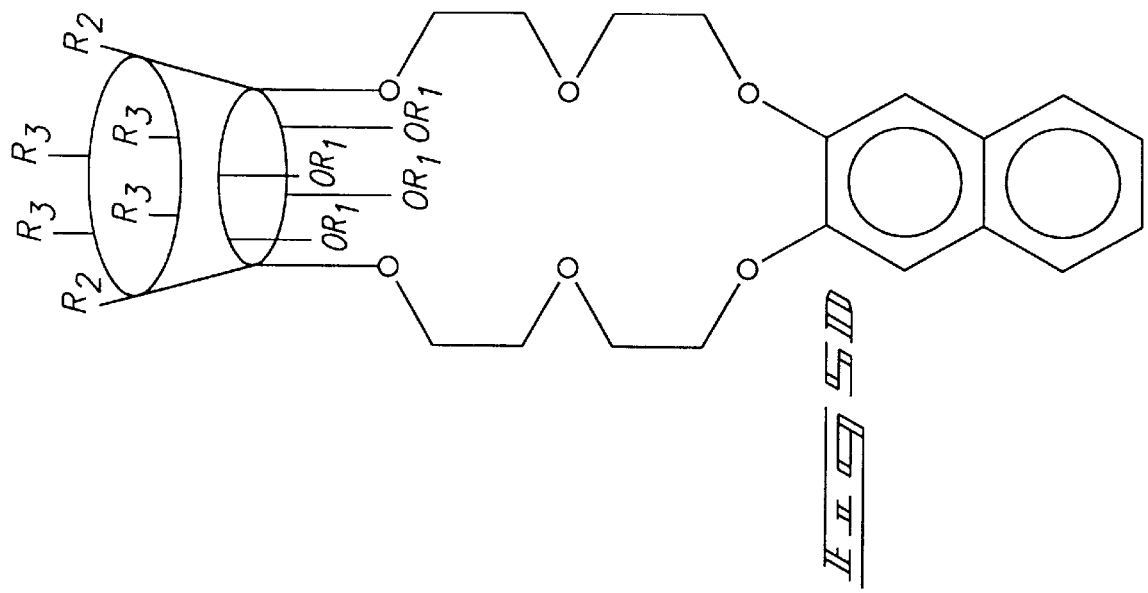
Figure 5C:
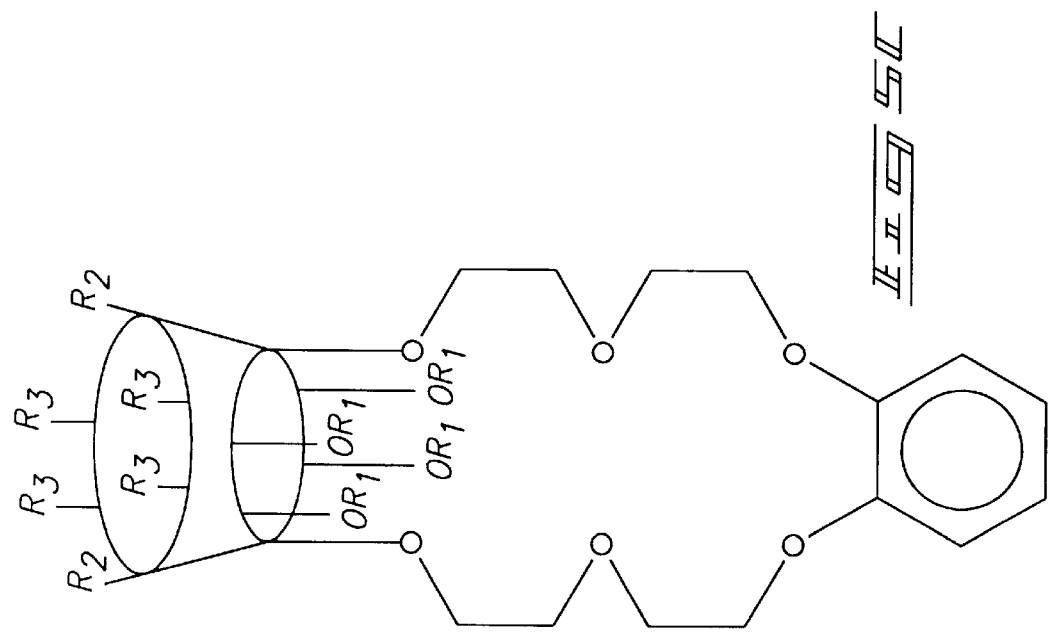
Figure 5F:
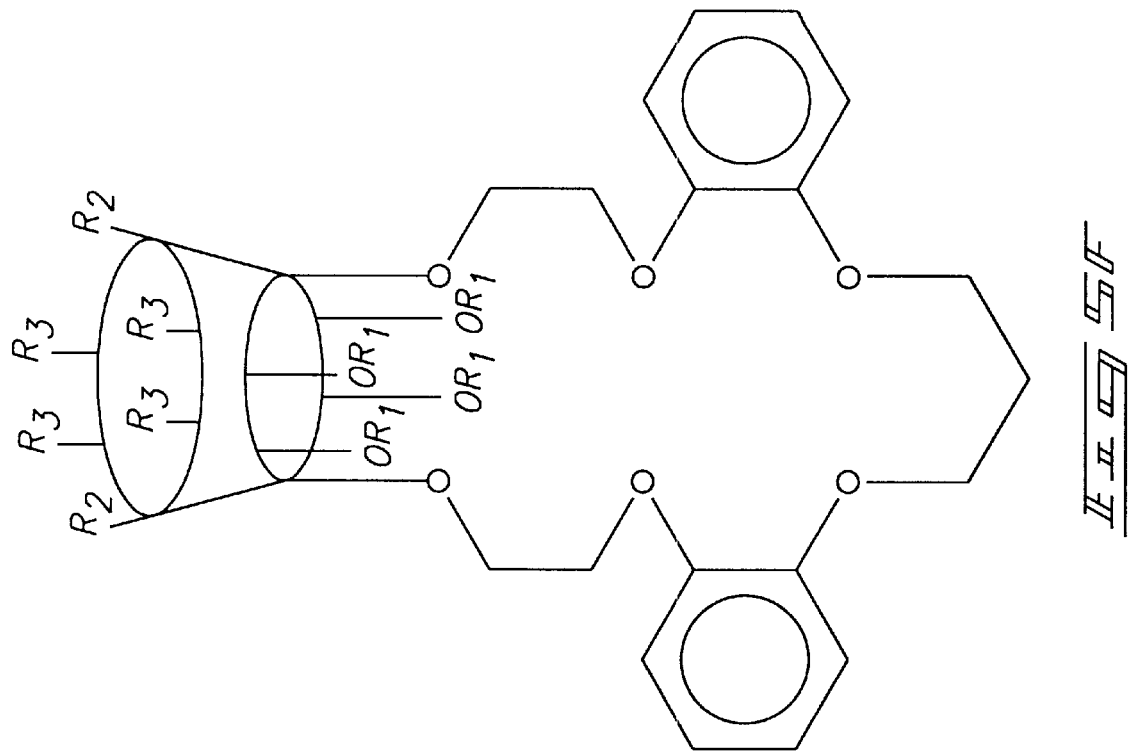
Figure 5E:
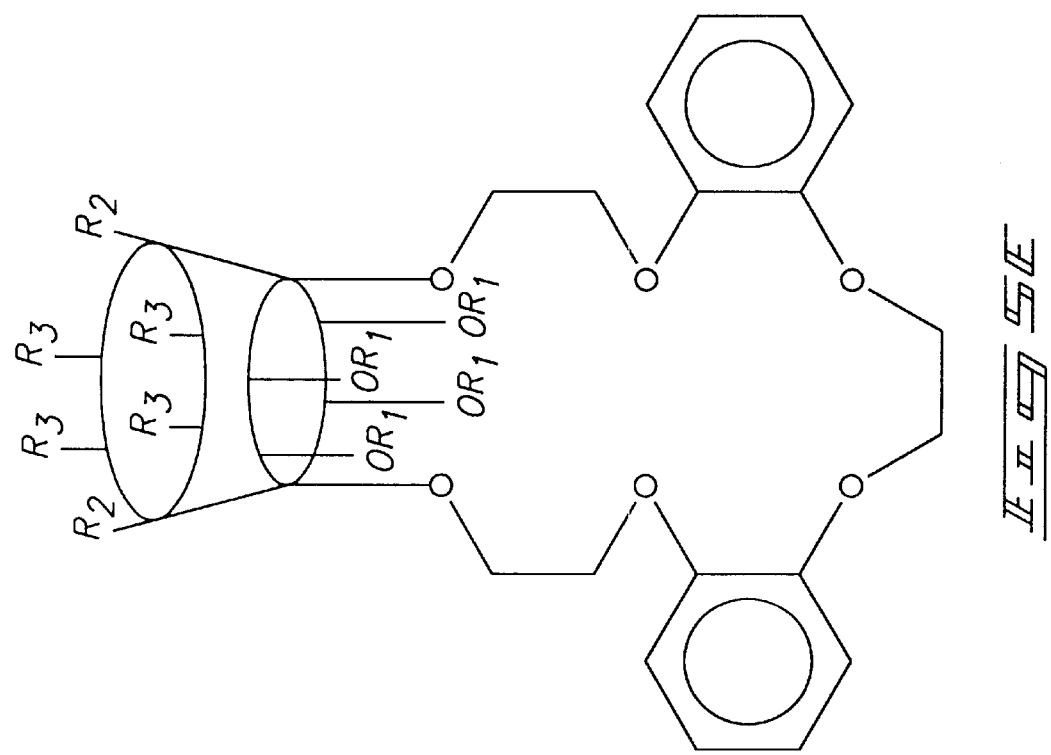
Figure 5G:
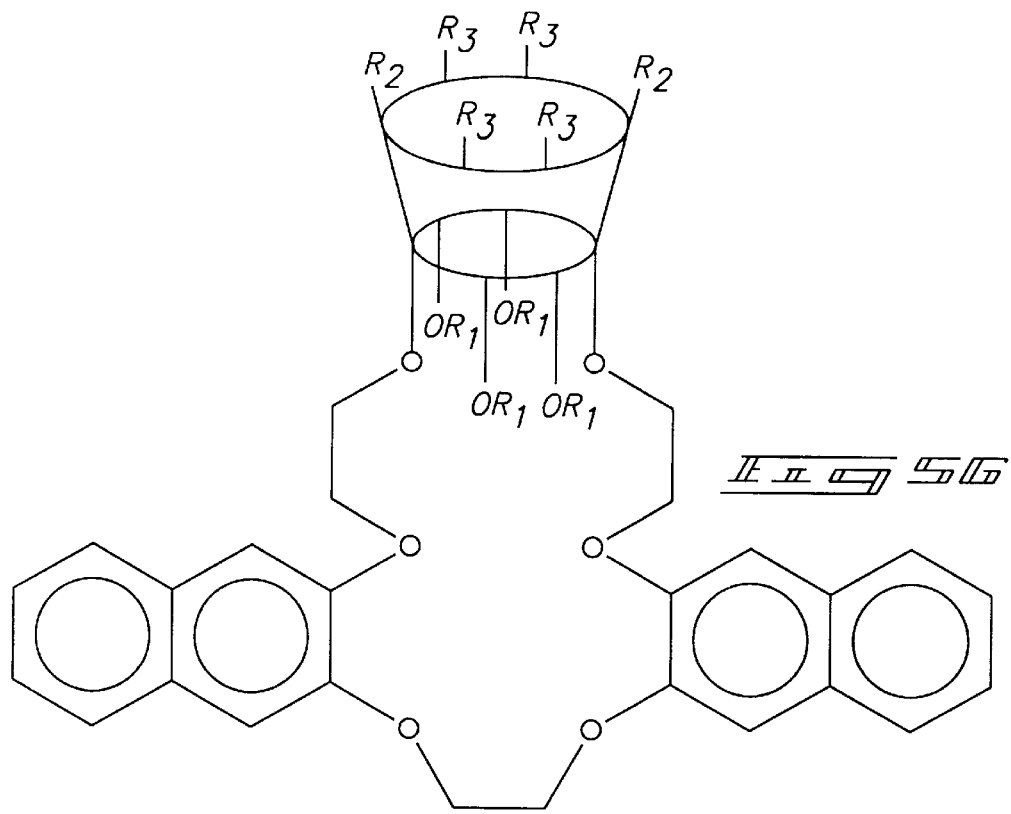
Figure 5H:
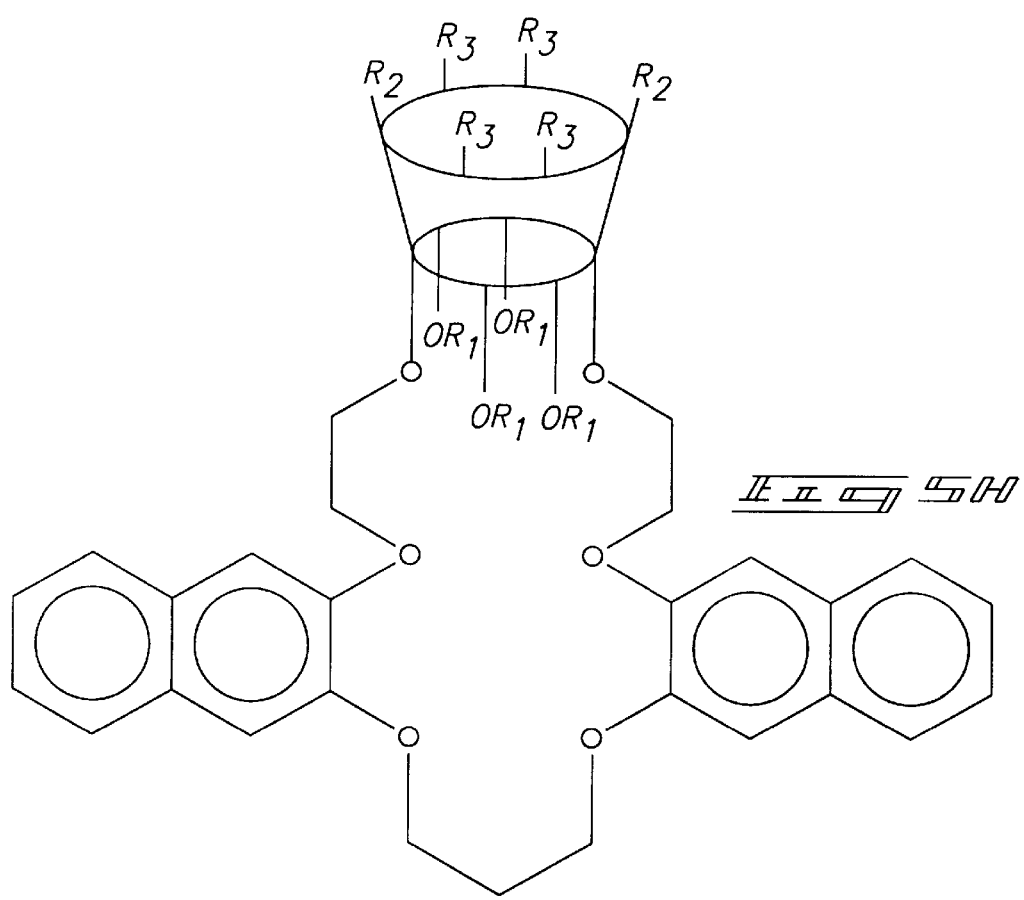
Figure 6A:
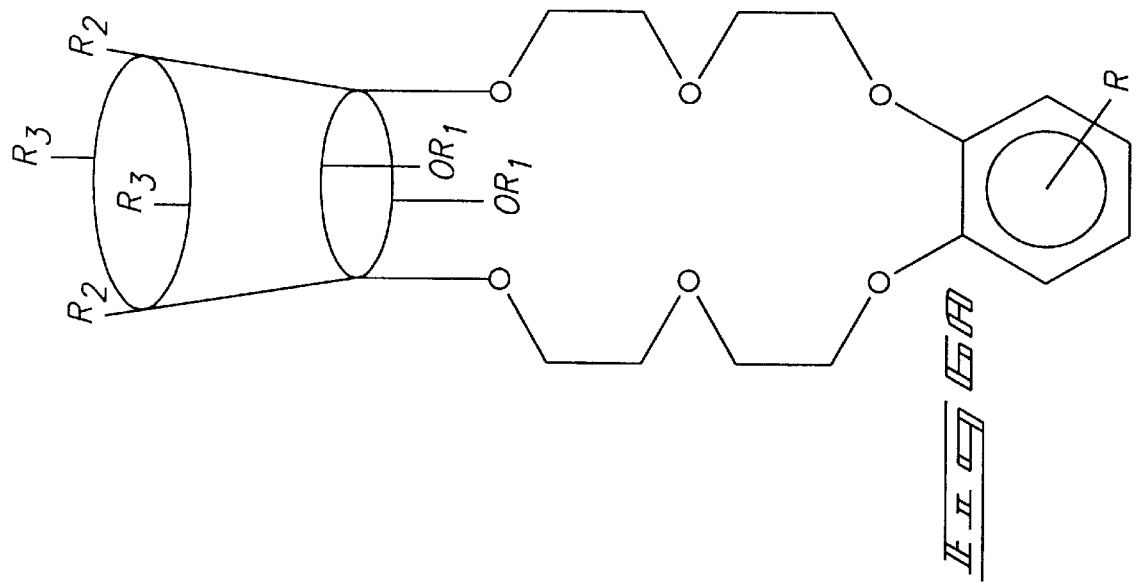
Figure 6I:
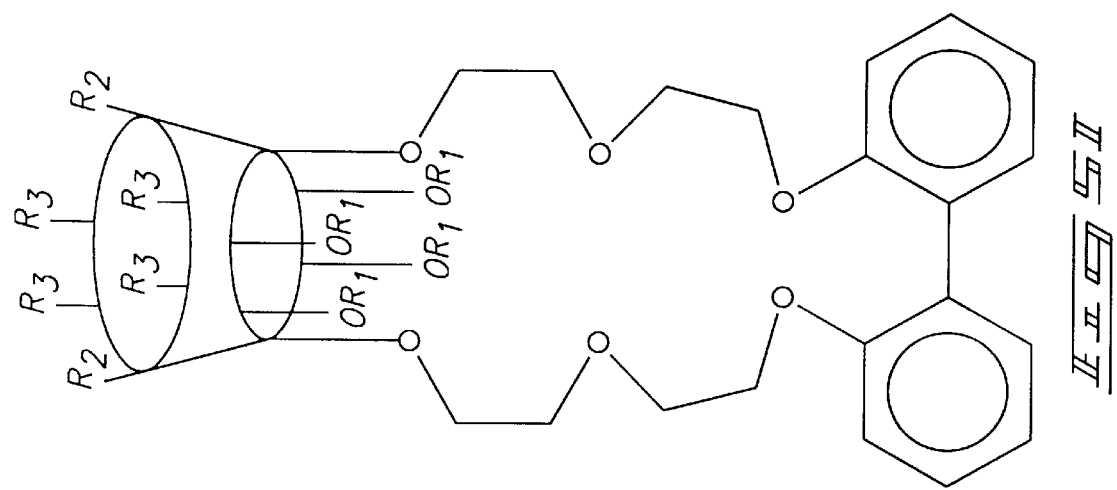
Figure 6C:
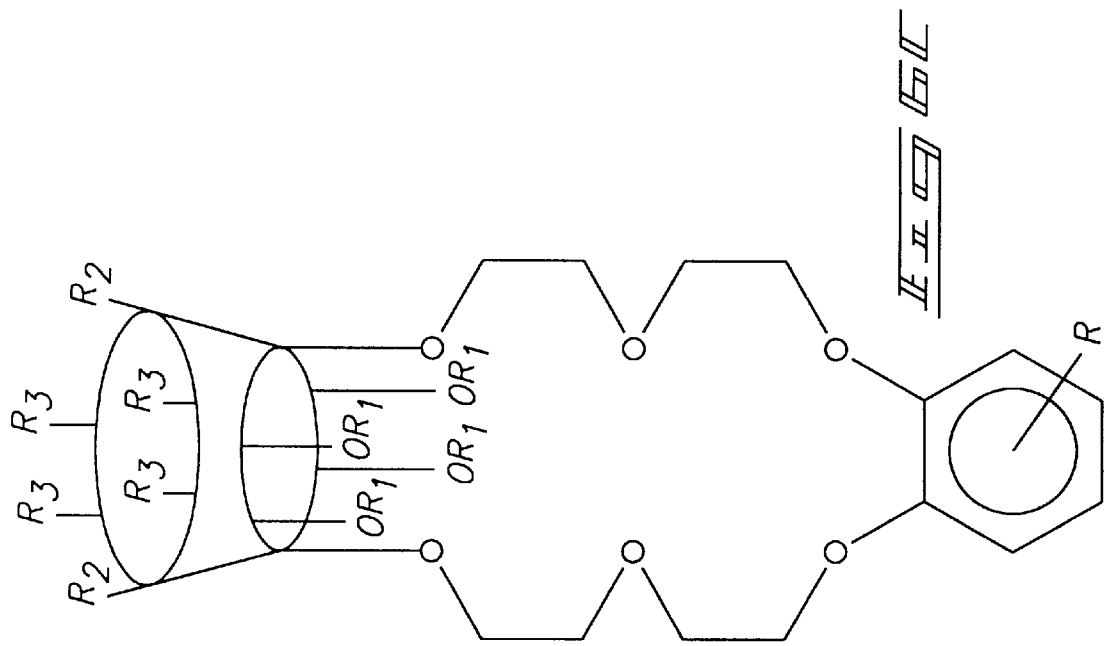
Figure 6B:
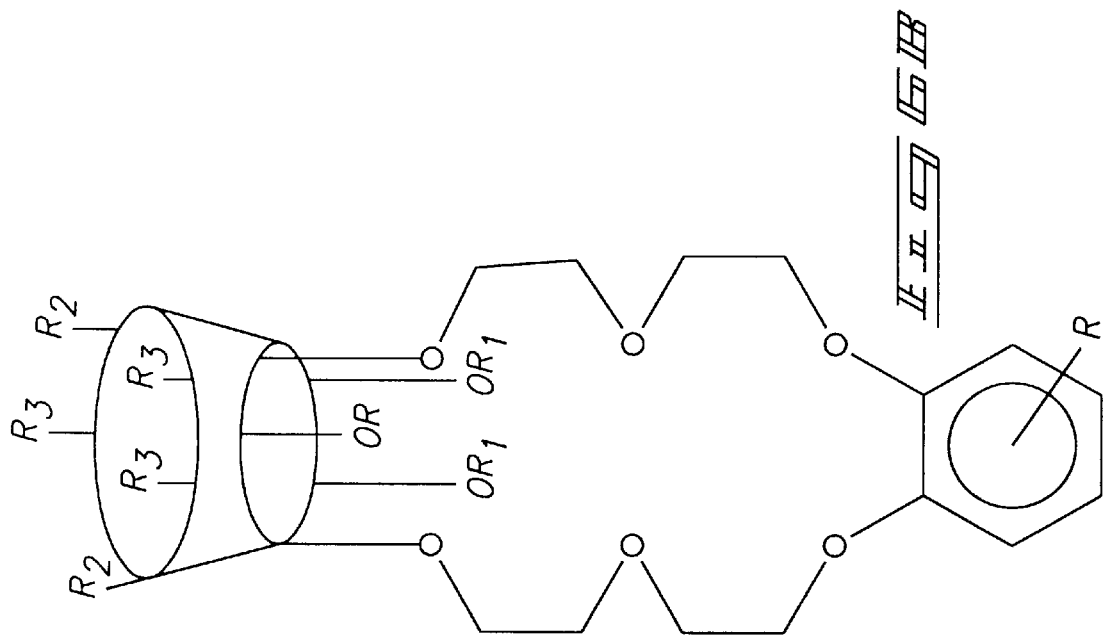

A method of synthesizing the calix[4]arene-crown-[6]-ether compound of FIGS. 1A and B is illustrated in FIG. 2. A starting calix[4]arene compound comprising t-butyl calix [4]arene (labeled "A") is mixed with a crown ether precursor (pentaethyleneglycol ditosylate) in benzene with KtBuO as a base. During the reaction, the pair of tosylated ends of the crown ether precursor react with a pair of phenolic hydroxyl groups of calix[4]arene compound "A" to convert the pair of phenolic hydroxyl groups to ether linkages. The ether linkages connect the crown ether precursor to calix[4]arene compound "A" to form a t-butyl-calix[4]arene-crown-[6]-ether compound (labeled "B").

Compound "B" is reacted with $BrCH_2COOEt$ in tetrahydrofuran (THF) using NaH as a base to convert a remaining pair of phenolic hydroxyl groups from "A" into a pair of esters and to thereby form "C". More specifically, "C" is formed as follows. To a stirred solution of "B" (1 mmol) in 40 mL of freshly distilled dry THF is added NaH (0.25 g, ca. 10 mmol) followed by ethyl bromoacetate (10 mmol). The reaction mixture is refluxed overnight under nitrogen, after which no starting material is detected on TLC plates ($SiO_2$, $CH_2Cl_2$/ethyl acetate=4:1 v/v). Most of the solvent is removed under reduced pressure, and the remaining residue is poured into a 2N HCl solution and extracted several times with methylene chloride. Each extraction yields an organic solution. The organic solutions are combined and washed with water. Subsequently, the solvent is removed under reduced pressure to yield a crude product. The crude product is recrystallized from ethanol to give colorless microcrystals of "C" at about a 78% yield.

Compound "C" is reacted in ethanol-$H_2O$, using NaOH as a base, to convert the esters to acids and to thereby form t-butyl-calix[4]arene-crown-[6]-ether dicarboxylic acid ("D"). More specifically, "C" is converted to "D" as follows. To "C" (1 mmol in 30 mL of ethanol) is added 3N NaOH (20 mL), and the resulting solution is refluxed for 24 hours. Most of the ethanol is then removed under reduced pressure to form a reduced solution. An excess of 2N HCl is added to the reduced solution to precipitate a white solid ("D"). The crude white solid is extracted with chloroform to remove any possible inorganic salts. The resulting residue is recrystallized from ethanol-$H_2O$. Thin layer chromatography (TLC) analysis reveals a single spot ($SiO_2$, $CH_2Cl_2$/MeOH= 9:1 v/v). The yield from this reaction is about 73%.

Subsequently, in a step which is not shown, "D" can be combined with $Ra^{2+}$ to incorporate the $Ra^{2+}$ within compound "D".

Although the above description is specific for t-butyl-calix[4]arene-crown-[6]-ether compounds, it is recognized in accordance with the present invention that other calix[n] arene-crown-[m]-ether compounds may be utilized for binding radionuclides. Specifically, compounds of the general class calix[n]arene-crown-[m]-ether, wherein n and m are integers greater than 3, are recognized as being suitable for binding radionuclides. Several such compounds are identified in FIGS. 3–6.

In FIG. 3, n=0, 1, 2 or 3,

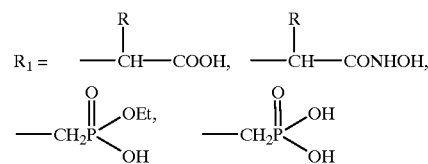

$R_2$=alkyl or H, and
$R_3$=alkyl or H.
In FIG. 4,

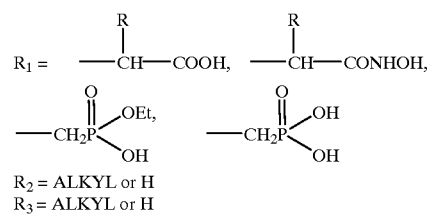

$R_2$ = ALKYL or H
$R_3$ = ALKYL or H

In FIG. 5,

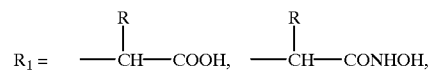

-continued

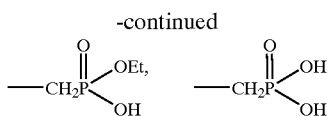

$R_2$=alkyl or H, and
$R_3$=alkyl or H.
In FIG. 6,

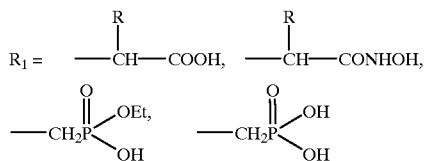

$R_2$=alkyl or H,
$R_3$=alkyl or H, and
R=Cl, Br, I, CHO or $NH_2$.

Also, to render the compounds of FIG. 6 water soluble, $R_2$ and/or $R_3$ can be polar and/or charged groups, such as: $-SO_3H$, $-SO_2N(CH_2CH_2OH)_2$, $-N^+R$, polyethyleneoxy chains, $-SO_2NHCH_2C(O)N(CH_2CH_2OH)_3$, or $-PO_3^-$ The compounds of FIGS. 3–6 comprise calix[n]arene portions, wherein n is an integer greater than 3 and less than 7. The compounds further comprise crown-[m]-ether portions, wherein m is an integer greater than 3 and less than 7. Several of the compounds comprise aromatic rings. The aromatic rings can be utilized to stiffen the crown-[m]-ether portion of a calix[n]arene-crown-[m]-ether compound to modify the affinity of the crown-[m]-ether portion for a selected radionuclide.

Figure 7E:
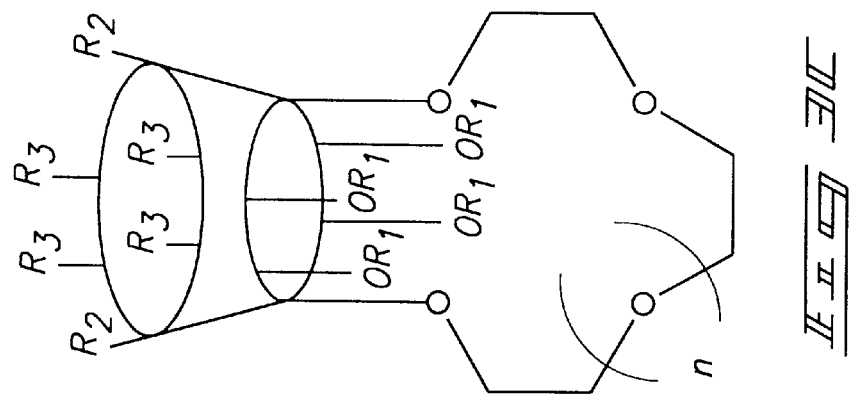
FIG. 7 illustrates a process for making one of the compounds of FIG. 6.
Figure 7F:
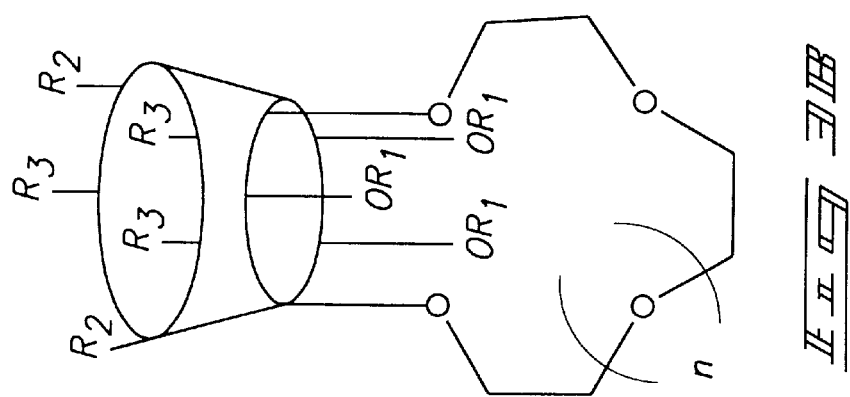
Figure 7G:
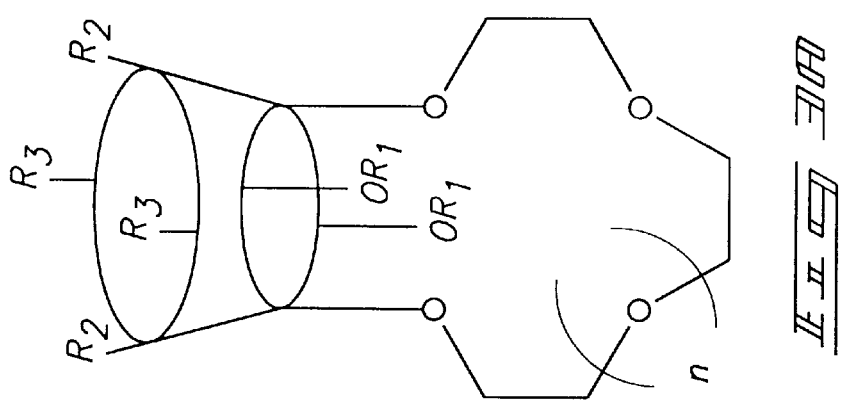
Figure 7A:
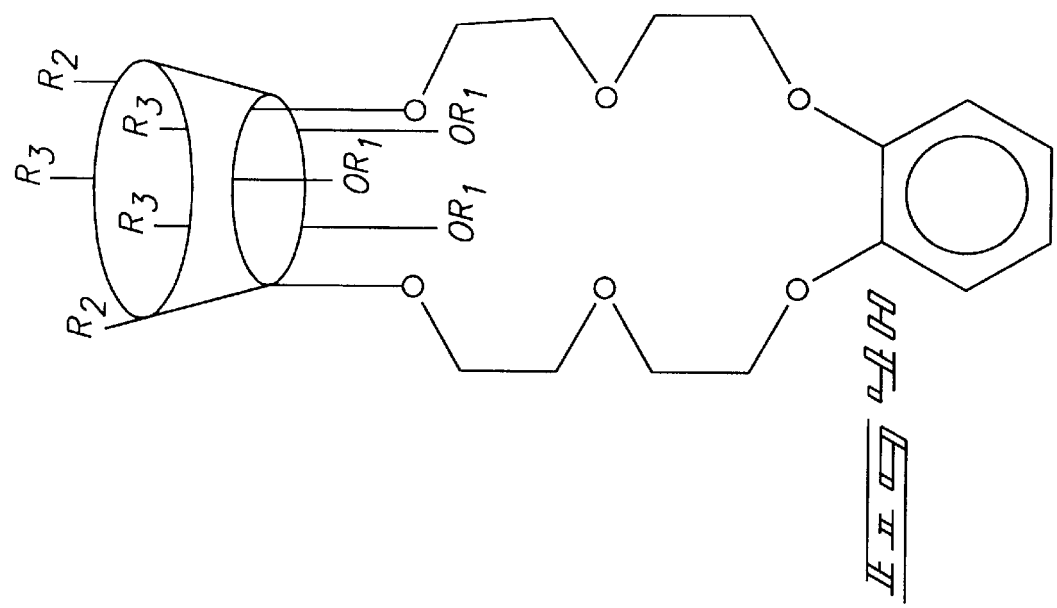
Figure 7B:
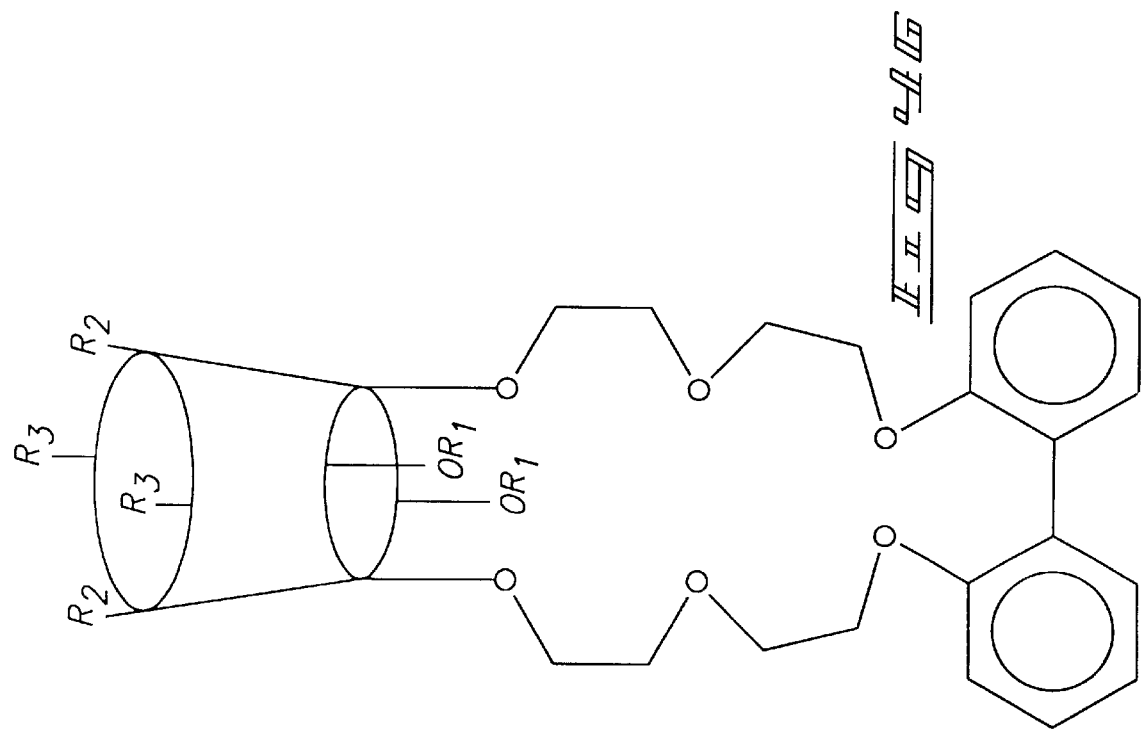
Figure 7:
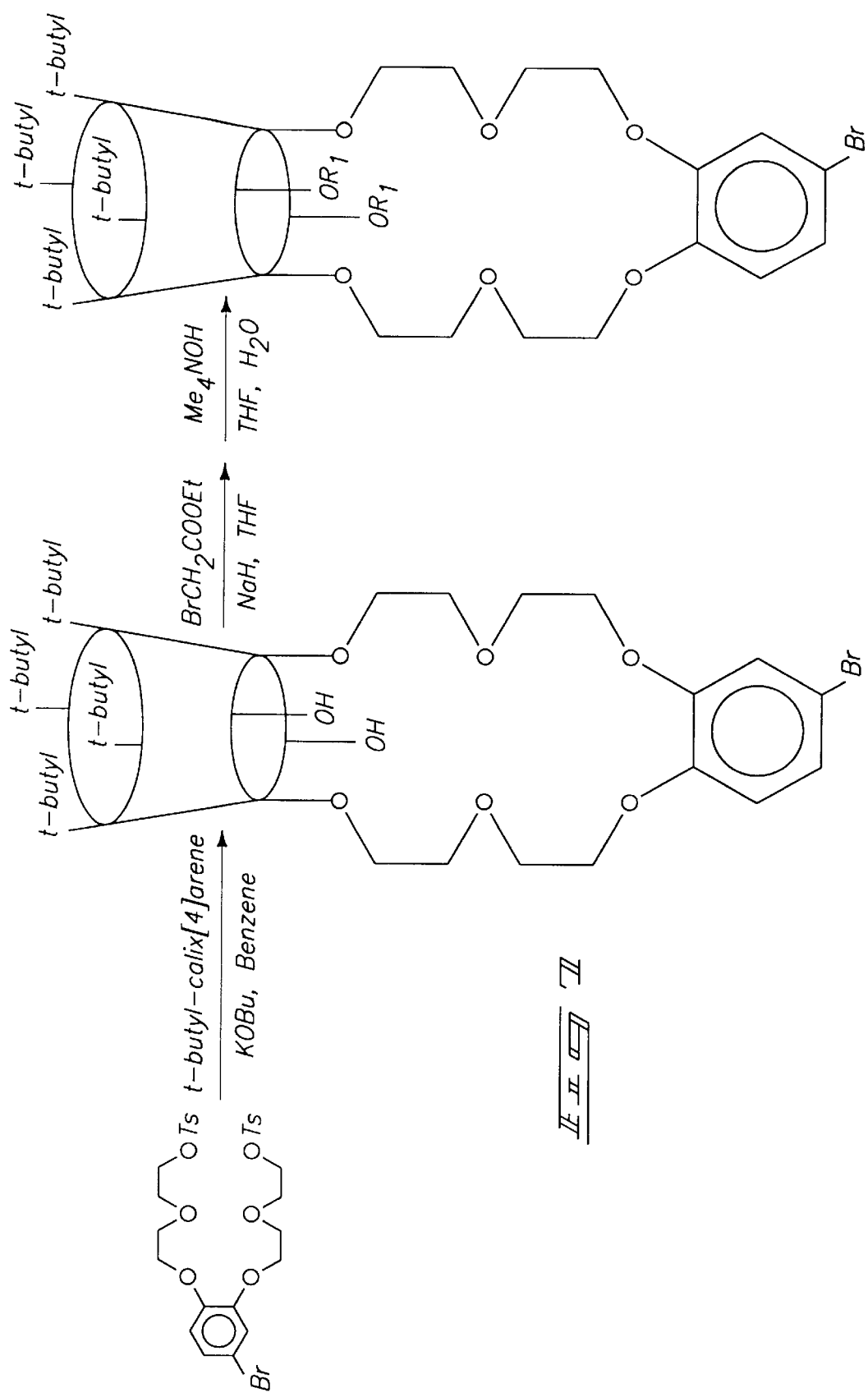

The compounds of FIGS. 3–6 can be synthesized by variations of the reaction scheme illustrated in FIG. 2. An example variation for synthesizing the compound labeled of FIG. 6A is illustrated in FIG. 7. In FIG. 7, $R_1$=$CH_2COOH$. The scheme in FIG. 7 varies slightly from that in FIG. 2, in that the final step for conversion of esters to acids utilizes $Me_4NOH$ in THF, rather than the sodium hydroxide in ethanol-$H_2O$ of FIG. 2. It is to be understood that either of the final steps of FIG. 2 or FIG. 7 may be utilized in a reaction scheme for conversion of esters to acids. Additionally, other methods known to persons of ordinary skill in the art for conversion of esters to acids could be utilized in place of the methods shown in FIGS. 2 and 7.

A calix[n]arene-crown-[m]-ether compound of the present invention can be utilized for a number of applications. For example, the compound can be utilized to selectively extract radionuclides from solutions comprising such radionuclides, such as radioactive waste. For instance, a calix[4]arene-crown-[6]-ether compound can be utilized to selectively extract $Ra^{2+}$ from samples comprising $Ra^{2+}$. After extraction of a radionuclide from a sample with a calix[n]arene-crown-[m]-ether compound, the radionuclide-calix[n]arene-crown-[m]-ether complex can be removed from the sample to clean the sample of radioactivity. The sample is then non-radioactive and can be disposed of by relatively low-cost procedures, rather than the high-cost procedures normally associated with disposal of radioactive waste. Also, the calix[n]arene-crown-[m]-ether complexing agent can be recycled under acidic conditions by extracting it into an organic phase.

Another example use of the calix[n]arene-crown-[m]-ether compounds of the present invention is to deliver radionuclides to specific biological targets. To utilize the compounds for such delivery of radionuclides, the compounds can be first joined to one or more chemicals specific to a target location. A class of chemicals known to have particular targeting abilities are antibodies. For instance, the monoclonal antibody referred to as B1-anti-CD20 (produced by Coulter Immunology, Inc.) is known to target specific cancer cells.

As antibodies are proteins, the calix[n]arene-crown-[m]-ether compounds of the present invention can be linked to antibodies utilizing conventional protein linking methods. To accomplish such linkage, functional groups specific for linking proteins can be provided on upper rim 14 (shown in FIG. 1B) of a calix[n]arene portion of a calix[n]arene-crown-[m]-ether compound. Example methods for forming such functional groups are described with reference to FIGS. 8–13.

Figure 8B:
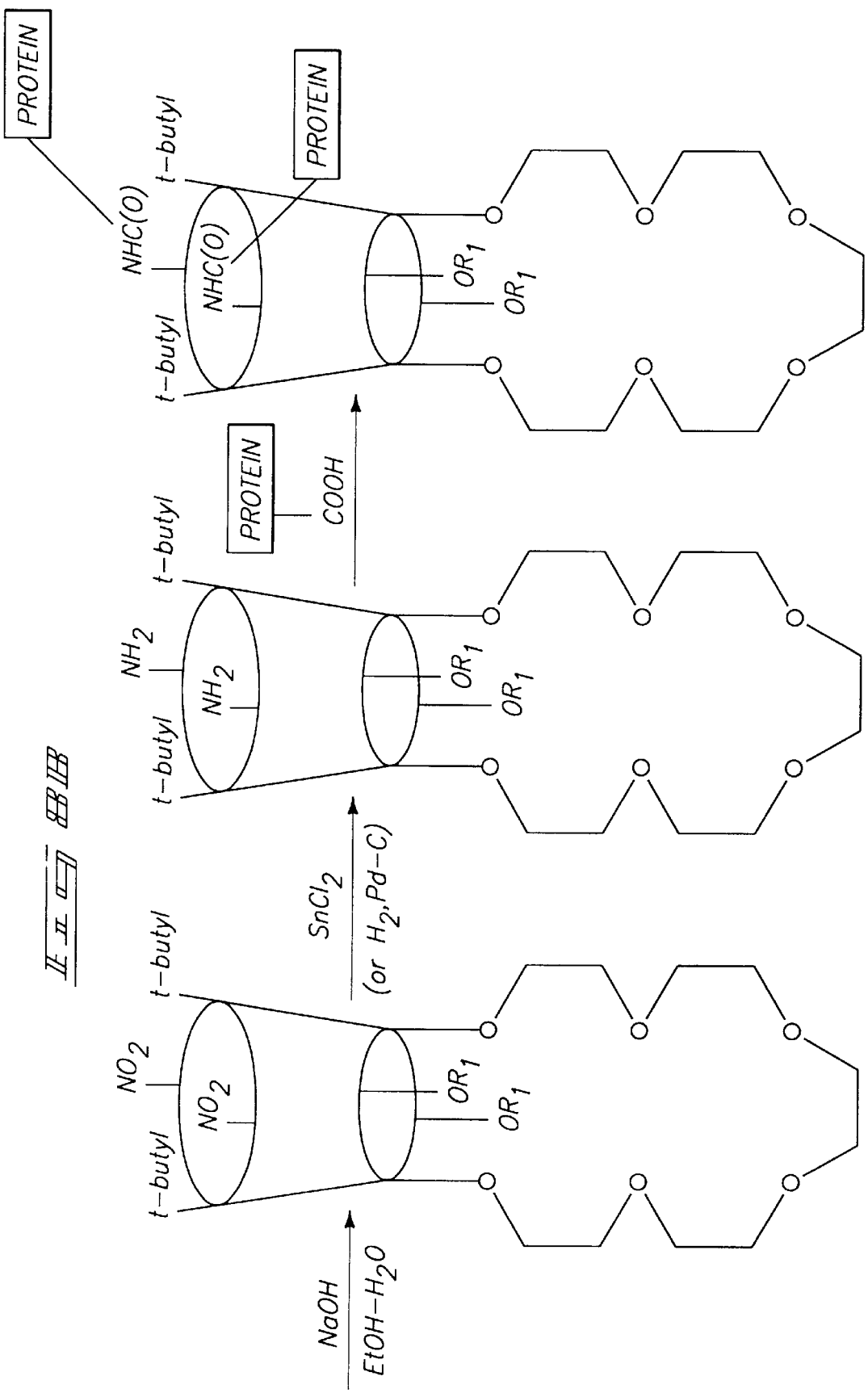
FIGS. 8A and B illustrate a process for forming amines on a calix[4]arene-crown-[6]-ether compound of the present invention.

Referring to FIGS. 8A and B, an amine linking group can be formed on a calix[n]arene-crown-[m]-ether compound of the present invention by a synthetic route utilizing ipso-nitration. First, $AlCl_3$ is utilized to convert two t-butyl groups of t-butyl-calix[4]arene-crown-[6]-ether to hydrogens. Next, nitration is accomplished with $HNO_3$–HOAc/$CH_2Cl_2$ at 0° C. Next, esterification and subsequent hydrolysis are conducted. Then, nitrate groups are reduced to amines. After the amine is formed, it can be attached to desired antibodies, or other proteins, through a peptide bond to a carboxylic acid group of the protein. Proteins contain carboxylic acid groups at their C-terminus, and also as side chains of various amino acids. Methods of forming peptide bonds between amine groups and carboxylate groups are known to persons of ordinary skill in the art.

In FIGS. 8A and B,
R=$CH_2COOEt$, and
R=$CH_2COOH$.

Figure 9A:
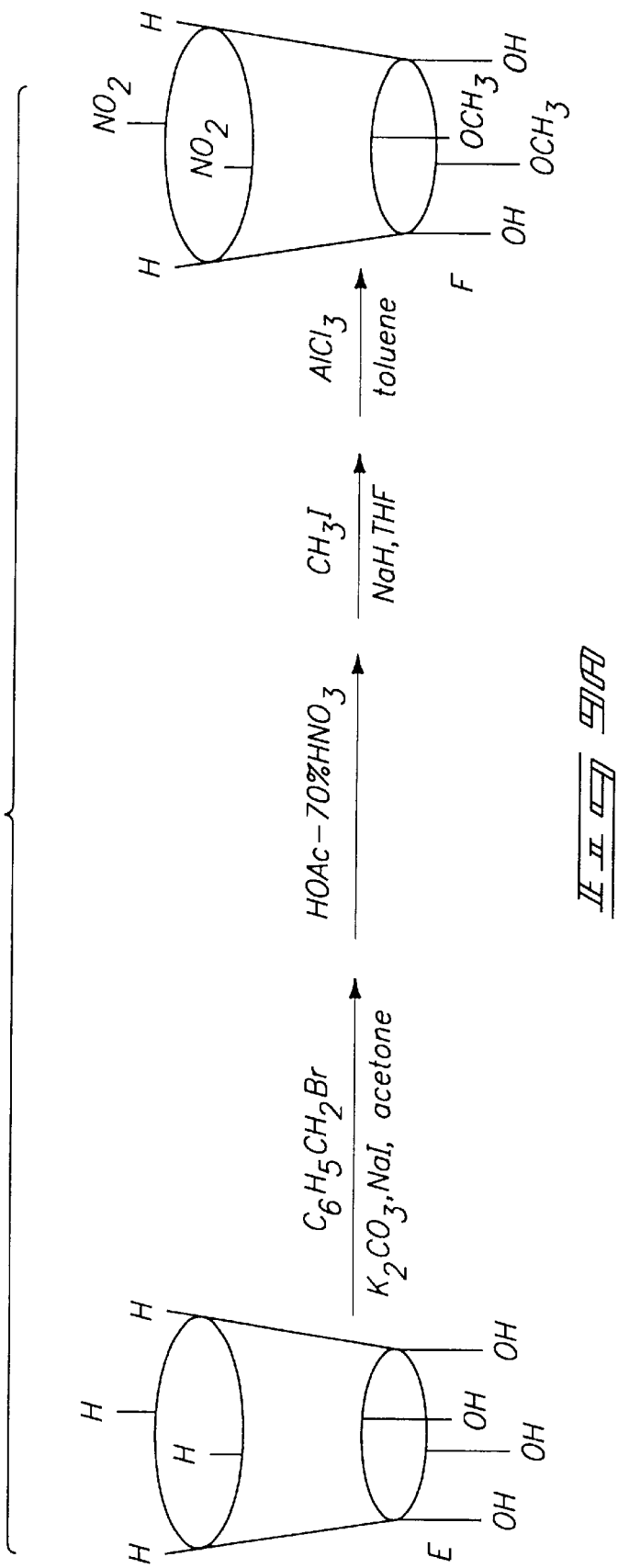
FIGS. 9A–C illustrate a process for forming amines on a calix[4]arene-crown-[6]-ether compound of the present invention.
Figure 9H:
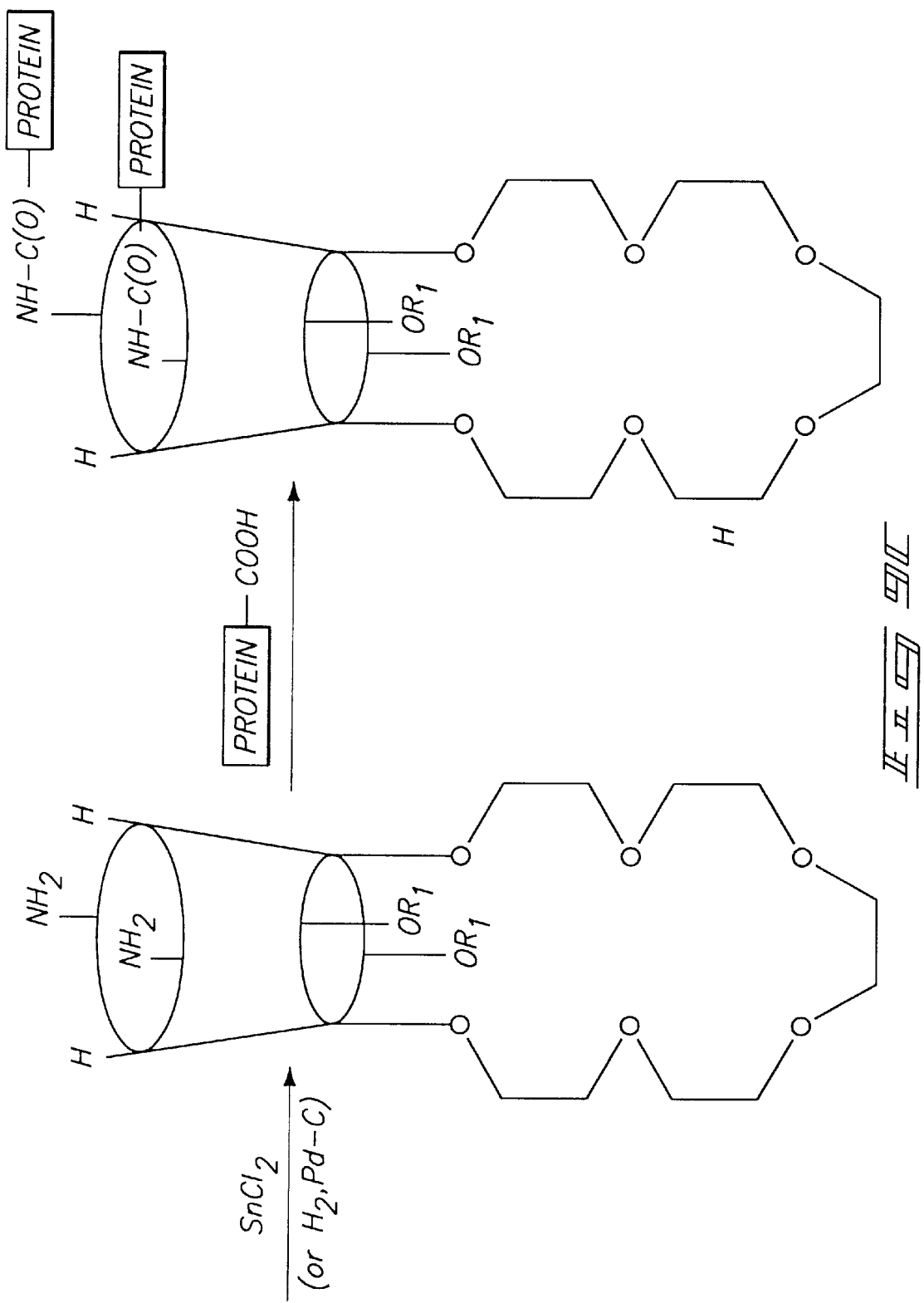

Referring to FIG. 9, another route for forming an amine linking group on a calix[n]arene-crown-[m]-ether compound of the present invention is illustrated. Initially, calix[4]arene (labelled "E") is converted to 5,17-dinitro-26,28-dimethoxycalix[4]arene-25,25-diol (labelled "F") by a procedure of Sharma and Gutsche. (See, Sharma and Gutshe, *J. Org. Chem.* 61, 2564 (1996).) The 5,17-dinitro-26,28-dimethoxycalix[4]arene-25,25-diol is the reacted with pentaethyleneglycol di-p-toluenesulfonate, with $Cs_2CO_3$ as a base and a template, to form 5,17-dinitro-26,28-dimethoxycalix[4]arene-crown-6-ether (labelled "G"). A pair of methyl groups of the 5,17-dinitro-26,28-dimethoxycalix[4]arene-crown-6-ether are removed by a reaction with iodotrimethylsilane, followed by esterification and hydrolysis to form compound "H", wherein $R_1$ is $CH_2COOH$. The nitro groups of compound "H" are reduced to form amines, which are utilized to form peptide bonds to proteins.

Figure 10A:
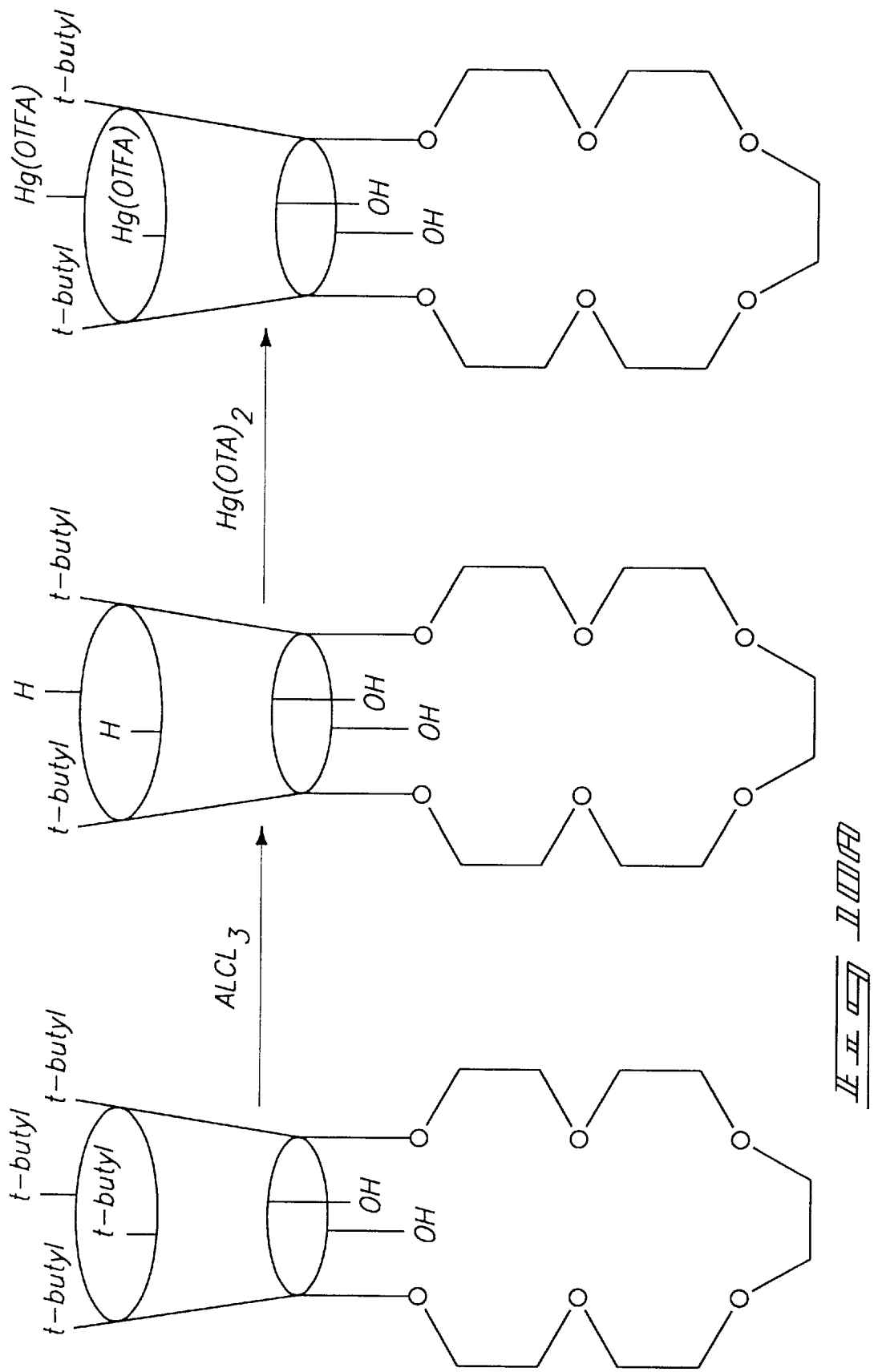
FIGS. 10A and B illustrate a process for forming iodine atoms on a calix[4]arene-crown-[6]-ether compound of the present invention.
Figure 10B:
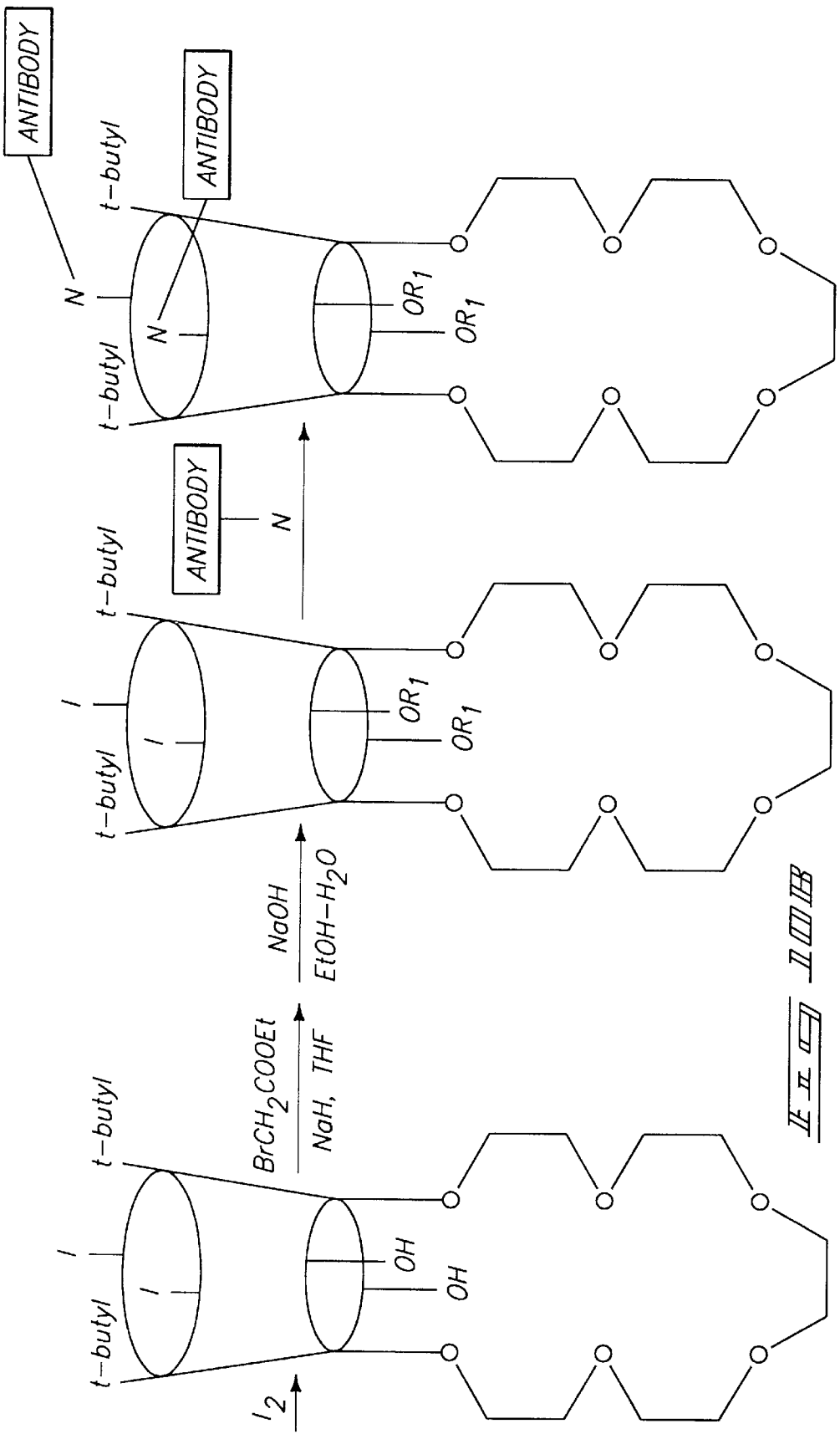

Referring to FIGS. 10A and B, a reaction scheme is illustrated for synthesis of calix[4]arene-crown-[6]-ether dicarboxylic acid with two iodide linkages on upper rim 14 (shown in FIG. 1B). The synthesis comprises Lewis acid catalyzed selective removal of two t-butyl groups para to free hydroxyl groups followed by treatment with mercury trifluoroacetate. After the mercury trifluoroacetate treatment, the dimercury compound smoothly reacts with $I_2$ to form a diiodo-calix[4]arene-crown-[6]-ether compound. Subsequently, esterification and hydrolysis are conducted to convert hydroxyl groups of the diiodo-calix[4]arene-crown-[6]-ether compound to carboxylic acids. An antibody can be attached to the calix[4]arene-crown-[6]-ether compound by displacing one of the iodo groups with an N-terminus amino group of the antibody. The iodo group can be displaced by an N-terminus amino group of the antibody utilizing conventional methods. In FIG. 10, $R_1=CH_2COOH$.

Figure 11B:
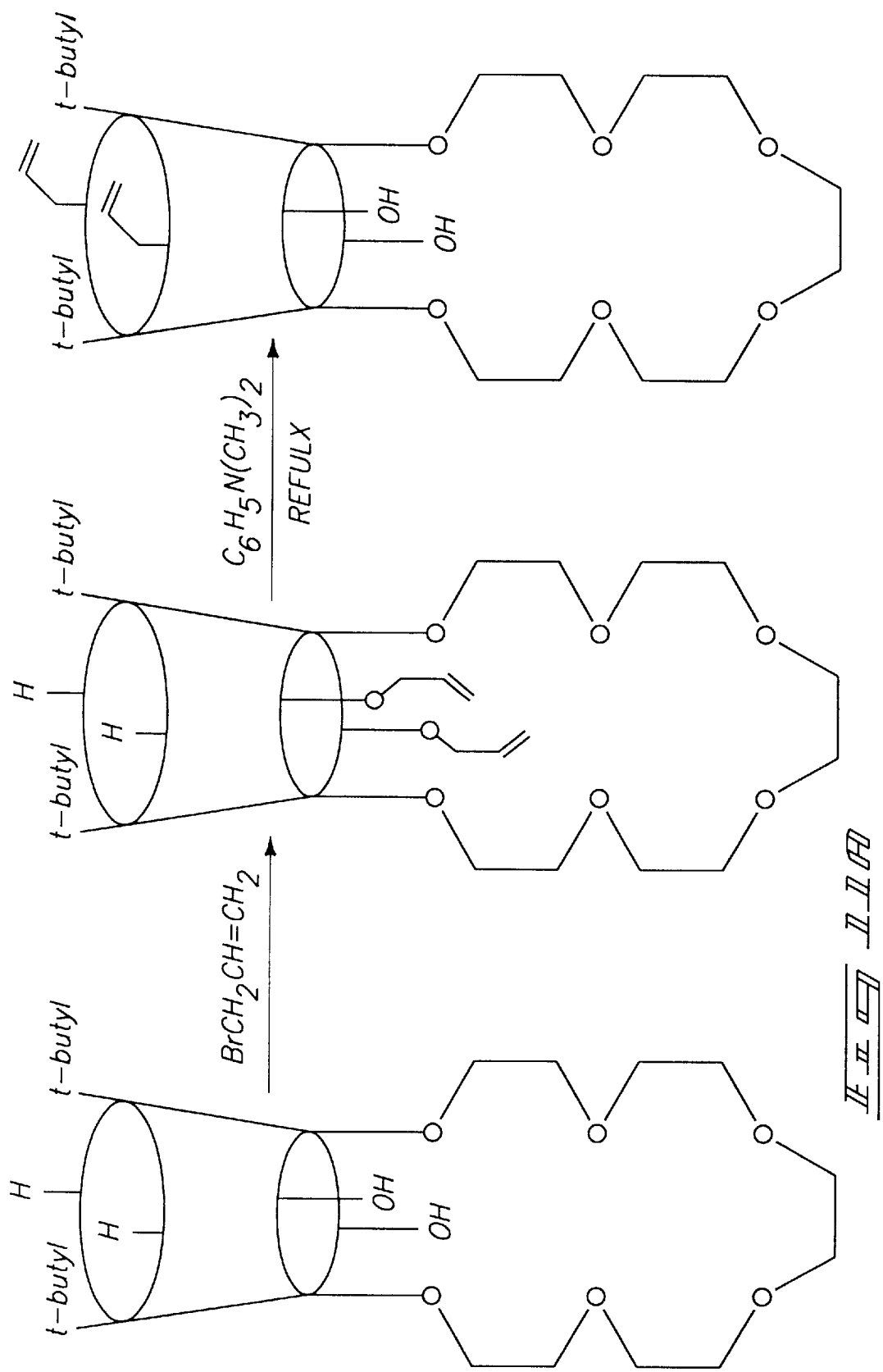
FIGS. 11A and B illustrate a process for forming alkyl derivatives of a calix[4]arene-crown-[6]-ether compound of the present invention.

Referring to FIGS. 11A and B, a para-Claisen rearrangement route for synthesis of calix[4]arene-crown-[6]-ether dicarboxylic acids with different linkers on upper rim 14 (shown in FIG. 1B) is illustrated. A selectively dealkylated calix[4]arene-crown-[6]-ether compound is converted to p-dibutyl-calix[4]arene-crown-[6]-diallyl ether. The p-dibutyl-calix[4]arene-crown-[6]-diallyl ether is heated in refluxing N,N-dimethylanilin. Such refluxing causes the p-dibutyl-calix[4]arene-crown-[6]-diallyl ether to undergo a para-Claisen rearrangement to produce p-diallyl-dibutyl-calix[4]arene-crown-[6]-ether. Subsequent esterification and hydrolysis produce p-diallyl-dibutyl-calix[4]arene-crown-[6]-ether dicarboxylic acid. The diallyl group can then be converted to a variety of functional groups. Such functional groups include oxoethyl, hydroxyethyl, bromoethyl, azidoethyl, aminoethyl, cyanoethyl, and formyl compounds. All of such functional groups can be utilized for linking the calix[4]arene-crown-[6]-ether dicarboxylic acid to proteins utilizing conventional methods.

Figure 11B:
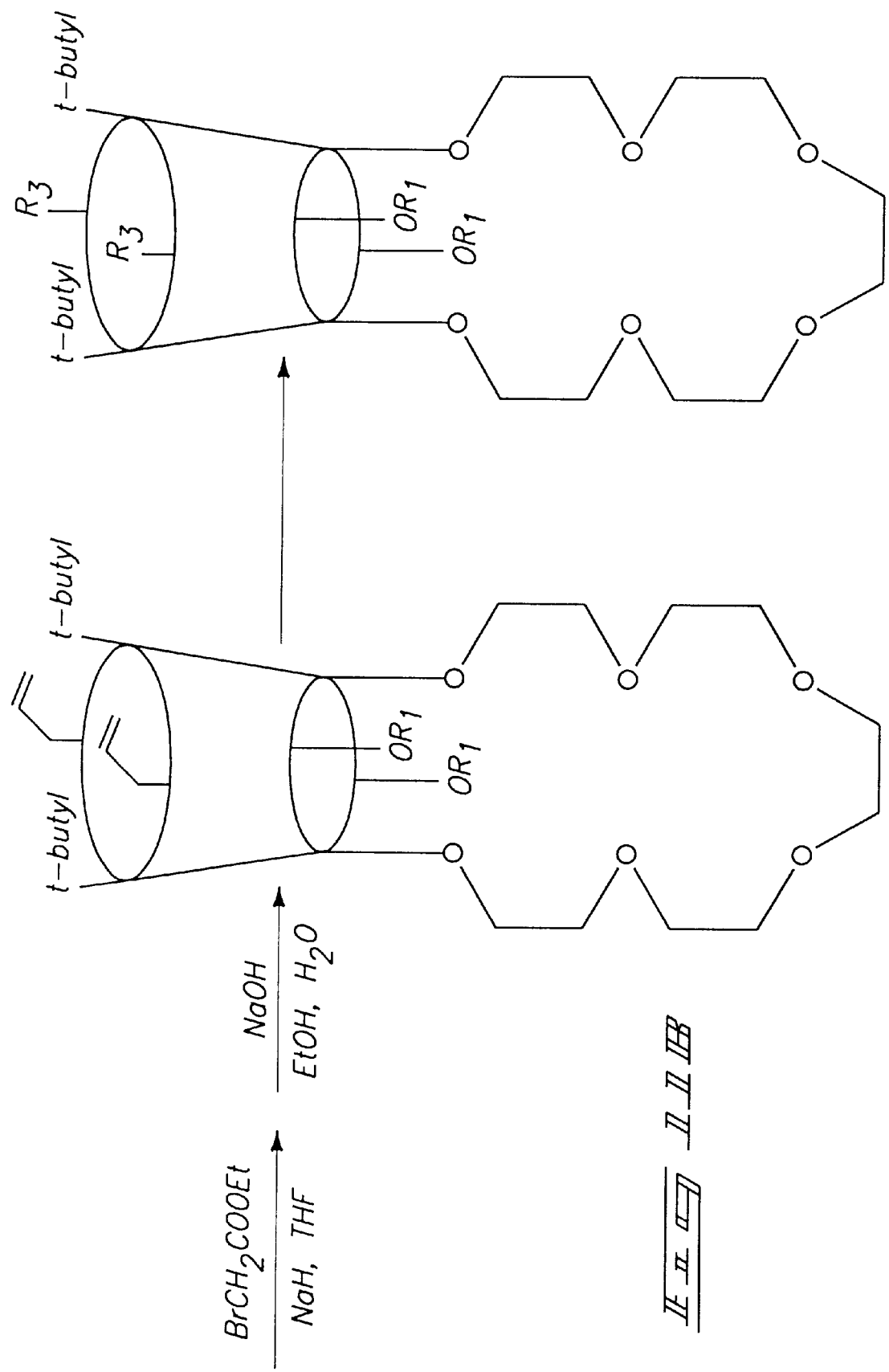
Figure 12A:
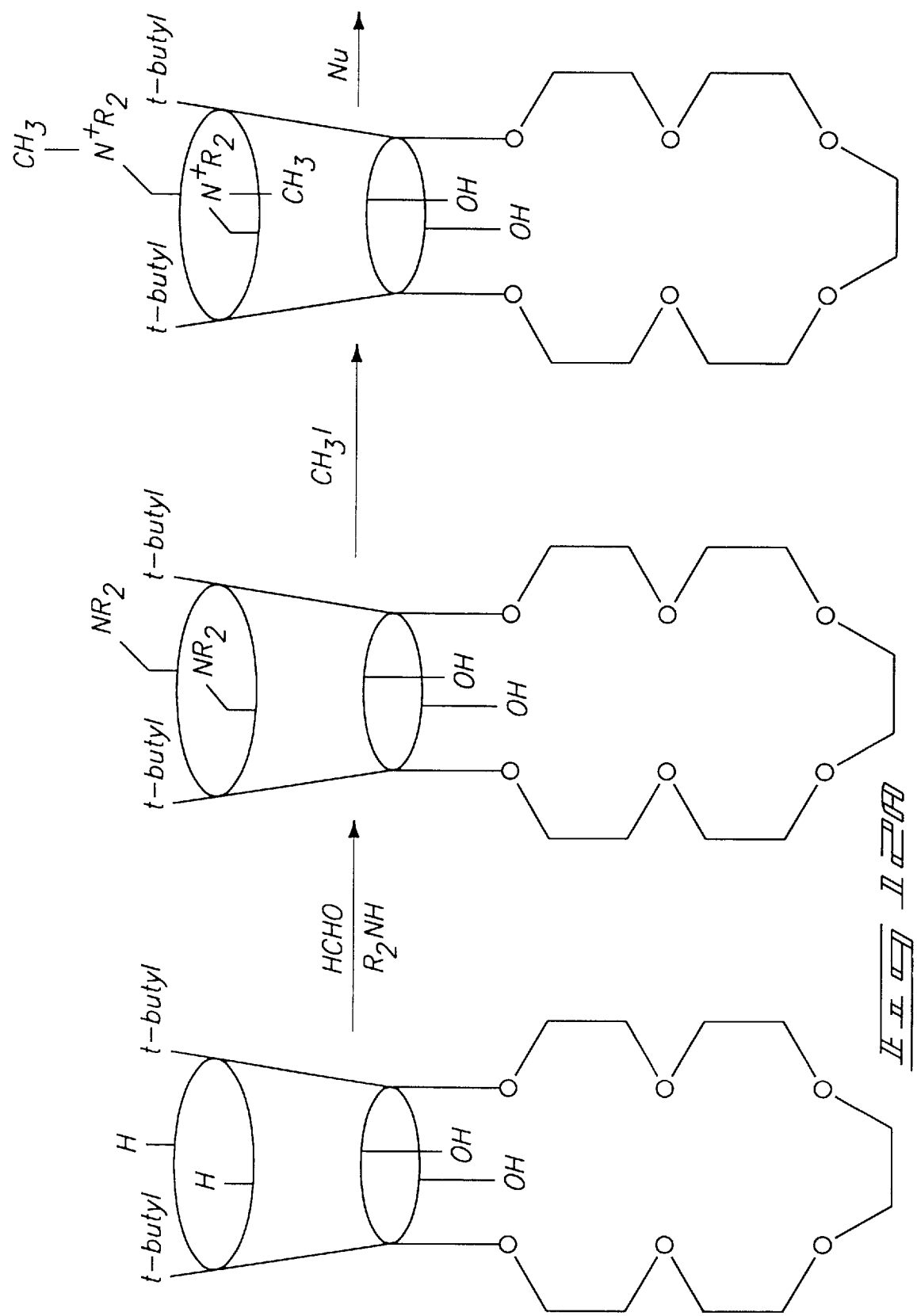
FIGS. 12A and B illustrate a process for attaching nucleophiles to a calix[4]arene-crown-[6]-ether compound of the present invention.

In FIG. 11,
$R_1=CH_2COOH$; and
$R_3=CH_2CHO$
$CH_2CH_2OH$
$CH_2CH_2Br$
$CH_2CH_2N_3$
$CH_2CH_2NH_2$
$CH_2CH_2CN$
CHO Referring to FIGS. 12A and B, a p-Quinonemethide route for synthesis of calix[4]arene-crown-[6]-ether dicarboxylic acid with different linkers on upper rim 14 (shown in FIG. 1B) is illustrated. First, a Mannich-type reaction is utilized to produce p-dialkylaminomethylcalix[4]arene. Subsequent addition of methyl iodide converts the amino groups to corresponding quaternary ammonium compounds. The quaternary ammonium compounds are treated with two equivalents of a nucleophile to create a $CH_2$-nucleophile substituted calix[4]arene-crown-[6]-ether dicarboxylic acid.

Figure 12B:
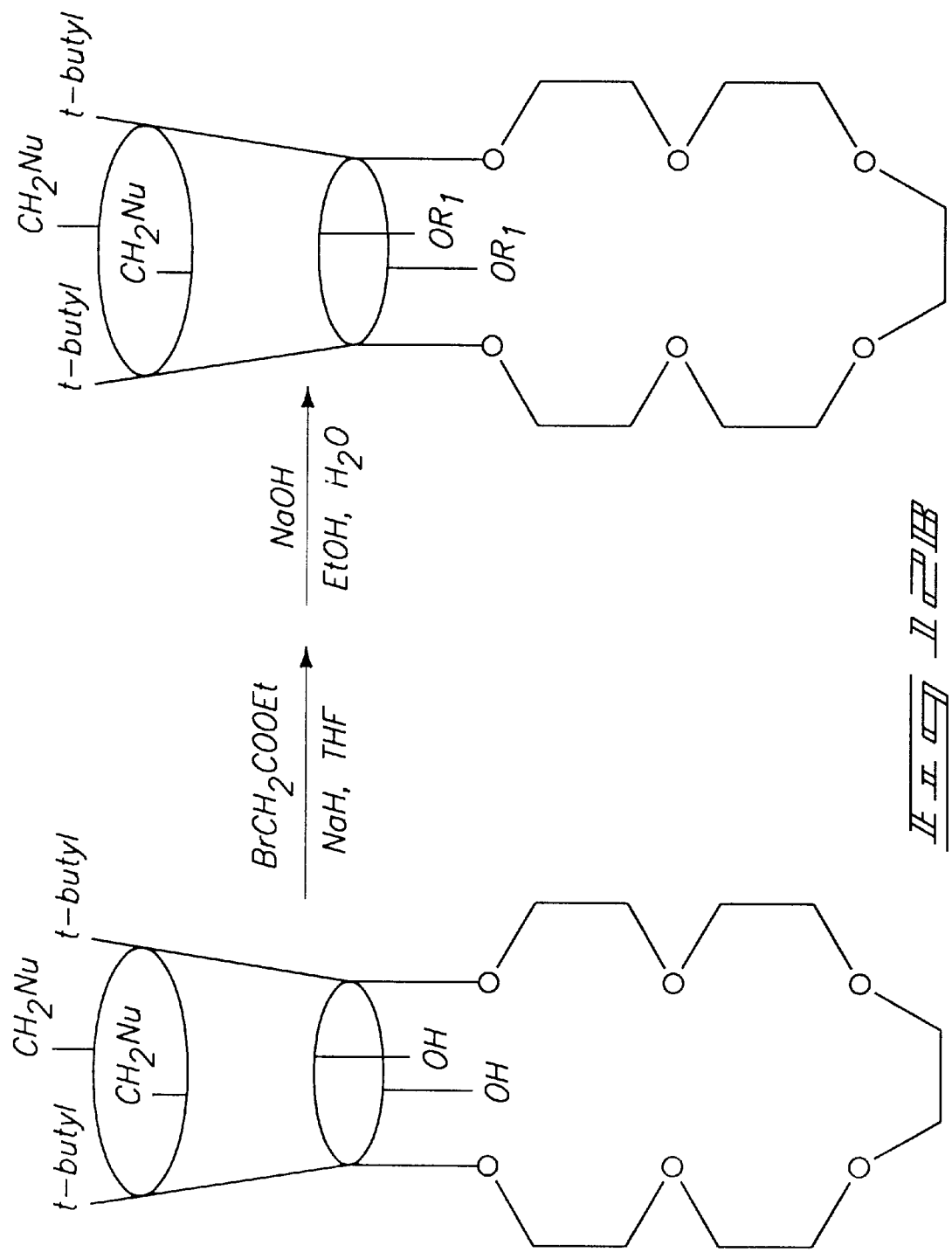
Figure 28:
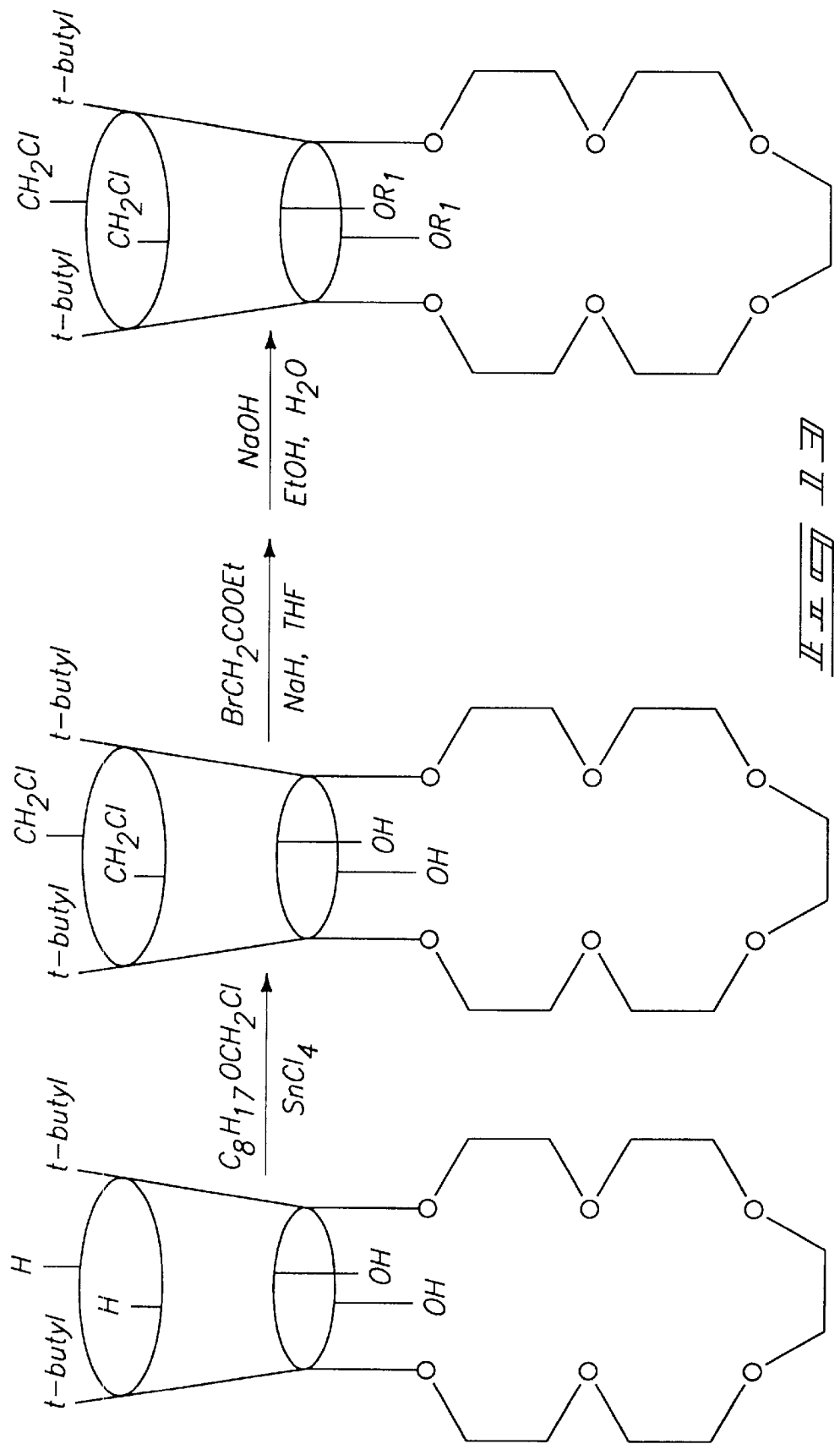

In FIG. 12,
$R_1=CH_2COOH$; and
Nu=OR, CN, CH(COOEt)$_2$
$CH(NO_2)$ (COOEt), $C_2H$ Cl,
CHO, $NO_2$,Br Referring to FIG. 13, a p-chloromethylation route for providing linking groups on an upper rim 14 (shown in FIG. 1B) of a calix[4]arene-crown-[6]-ether dicarboxylic acid is illustrated. A selectively dealkylated calix[4]arene-crown-[6]-ether compound is treated with octyl chloromethyl ether and $SnCl_4$ to form a p-chloromethyl calixarene compound. The p-chloromethyl calixarene compound is esterified and then treated with base to form calix[4]arene-crown-[6]-ether dicarboxylic acid with two choloromethyl groups on its upper rim. The chloromethyl groups can be utilized to attach the calixarene compound to an antibody by conventional methods. In FIG. 13, $R_1=CH_2COOH$.

The reactive groups formed by the reactions of FIGS. 8–13 can be utilized to link to an antibody through various groups on the antibody, including, for example, phenolic side chains of tyrosine, ε-amino groups of lysine, cysteine sulfhydryl groups, carboxy terminus carboxylate, and an N-terminus amino group. For example, the linkers comprising diazonium salts can form azo linkages with tyrosine, the linkers comprising isothiocyanates can react with the ε-amino groups of lysine, and the linkers comprising alkylbromides can form linkages with the sulfhydryl groups. Methods utilizing the above-described reactive groups to bind to proteins are known to persons of ordinary skill in the art and can be found, for example, in Kozak, Waldmann, Atcher, and Gansow (1986) *Radionuclide-conjugated Monoclonal Antibodies: A Synthesis of Immunology, Inorganic Chemistry, and Nuclear Science*, in *Trends in Biotechnology*, pp. 259–264, published by Elsevier Science Publishers. The ε-amino group of lysines appear to be among the most useful for linking antibodies to molecules. Covalent binding to ε-amino groups can be achieved using isothiocyanatobenzyl, amino-caproic acid, or thiol conjugation with reduced disulfide linkage to a calix[4]arene-crown-[6]-ether compound. A length of an individual linker can be configured to enable an antibody bond to the linker to have sufficient freedom of movement to tightly bind to its antigen. Preferred linkers will provide from about 2 to about 4 carbon atoms between a linking functional group and an upper rim 14 (shown in FIG. 1B) of a calix[n]arene-crown-[m]-ether compound.

Several experiments have been conducted to ascertain the selectivity of compounds of the present invention for $Ra^{2+}$. The results of such experiments are described with reference to FIGS. 14A–D, 15, and Table 1. Referring to FIGS. 14A–D, a series of compounds "I"–"L" are illustrated, with $R_1=CH_2COOH$, and $R_2=R_3=$t-butyl. The compounds include a calix[4]arene-crown-[6]-ether dicarboxylic acid ("I"), tert-butyl-16-crown-5-carboxylic acid ("J"), acyclic-polyether-dicarboxylic acid ("K"), and a calix[6]arene-crown-[5]-ether compound ("L"). Compounds "I"–"L" were synthesized and measurements were conducted to determine the selectivity (preference for) and stability (binding strength) of the compounds for $Ra^{2+}$. Table I shows results of a two-phase solvent extraction of $Ra^{2+}$ by the four different compounds.

TABLE I

Percent Extraction Of Alkaline Earth Metal Ions From Water To $CHCl_3$ at pH = 8.9, and 25° C.[a]

Extractability (%)

| ionophore | $Mg^{2+}$ | $Ca^{2+}$ | $Sr^{2+}$ | $Ba^{2+}$ | $Ra^{2+}$ |
|---|---|---|---|---|---|
| "I" | 0 | 15.6 | 73.5 | 98.7 | 100 |
| "J" | 12.4 | 17.8 | 13.8 | 12.5 | 13.4 |
| "K" | 93.8 | 92.5 | 90.3 | 87.0 | 89.0 |
| "L"[b] | 0 | 3.72 | 45.6 | 92.0 | 92.5 |

[a] The extractability "0" means Ex % <0.1%, and "100" means Ex % ≥99.9%
[b] For ligand "L", the experiment was performed at pH = 7.30.

The distribution coefficients listed in Table I were calculated as a concentration ratio of complexed metal to uncomplexed metal. The results of the study show that the calix[4]arene-crown-[6]-ether dicarboxylic acid of the present invention ("I") exhibits selectivity for $Ra^{2+}$ over other divalent alkaline earth metal cations; greater binding strength compared to "J", "K" and "L"; and greater selectivity for $Ra^{2+}$ compared to "K".

Referring to FIG. 15, the selectivity of compounds "I" through "L" (shown in FIG. 14) as a function of pH is graphed. The pH of the aqueous phase was adjusted with succinic acid-$NH_4OH$ for pH-6, Tris-HCL for pH 7–9, and Tris-$Me_4$NaOH for pH over 10. As evidenced by the graph, compounds "I", "K" and "L" evidence high selectivity for radium at physiological pHs.

It is noted that the calix[4]arene-crown-[6] antibody complexes can be utilized for targeting a number of cells, and can be utilized both in vivo and ex vivo. For instance, the compounds can be utilized for targeting eukaryotic cells in vivo, provided that an antibody is generated which is specific for the eukaryotic cells. Additionally, the compounds can be utilized for ex vivo treatment of materials, such as body fluids. For example, a conventional process for removing cancer from bone marrow is to extract the bone marrow from a patient and to treat the marrow with radiation or chemicals to attempt to eliminate cancer from the marrow. The treated marrow is then returned to the patient. In a method of the present invention, the isolated marrow can be treated with antibodies attached to calix[n]arene-crown-[m]-ether compounds, with the antibodies being specific for cancer in the bone marrow. The marrow can then be returned to the patient's body. Such method has advantages over prior art methods. For example, as a method of the present invention locally treats cancer cells with radiation, rather than generally treating an entirety of the isolated bone marrow with radiation, there is less chance of damage to normal cells utilizing a method of the present invention. Also, as a method of the present invention localizes the radiation to the cancer cells, it is possible to provide a higher dose of radiation to the cancer cells while reducing damage to normal cells, than can be accomplished with conventional methods. Another example use of a process of the present invention is to treat cancer cells in vivo.

For treatments of cancer, Ra-223 is a particularly effective radionuclide as Ra-223 generates four alpha particles during its decay to lead-207. Alpha particles are generally more lethal to cells than beta particles (electrons), X-rays, or gamma rays generated by radioactive processes, and so are preferred particles for killing cancer cells. A decay scheme for Ra-223 is shown in FIG. 16.

Ra-223 is also a particularly effective radionuclide for treating cancer because Ra-223 has an optimum physical half life for in vivo treatment of cancer. The physical half life of radium-223 is about 11.4 days. Recent studies indicate that a relatively long physical half life (4 to 12 days) of an alpha emitter is most desirable for in vivo cancer treatment. Specifically, recent dosimetry modeling by Rao and Howell showed that alpha emitters were preferable to beta emitters for therapy effectiveness, and that the optimum physical half-life of the radionuclide is one-to-three times the biological retention half-time of a radiolabeled antibody in a tumor. (See, Rao and Howell, *Time-dose Fractionation in Radioimmunotherapy: Implications to Selection of Radionuclides, J. Nucl. Med.* 34(5):105p (1993); and Rao and Howell, *Time-Dose-Fractionation in Radioimmunotherapy: Implications for Selecting Radionuclides,* J. Nucl. Med. 34: 1801–1810 (1993).) The pharmacokinetics of continuous protein uptake in some targeted solid tumors extend over periods of time and the biological retention half-times of some antibodies in tumors may be long (4 to 6 days). Typical tumor retention half-times are 48–96 hours (two to four days), and therefore optimal physical half-lives are 2 to 12 days, with longer half-times being preferred over shorter half-times.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A radionuclide delivery system comprising:
    a calix[n]arene-crown-[m]-ether compound, wherein n is an integer greater than 3, and wherein m is an integer greater than 3, the calix[n]arene-crown-[m]-ether compound comprising at least two ionizable groups; and
    an antibody attached to the calix[n]arene-crown-[m]-ether compound.

2. The radionuclide delivery system of claim 1 wherein the antibody comprises a nitrogen, and wherein the calix[n]arene-crown-[m]-ether compound is attached to the antibody through a covalent bond to the nitrogen.

3. The radionuclide delivery system of claim 1 wherein the antibody comprises a sulfur, and wherein the calix[n]arene-crown-[m]-ether compound is attached to the antibody through a covalent bond to the sulfur.

4. The radionuclide delivery system of claim 1 wherein the antibody comprises a phenolic group, and wherein the calix[n]arene-crown-[m]-ether compound is attached to the antibody through a covalent bond to the phenolic group.

5. The radionuclide delivery system of claim 1 wherein the antibody comprises a lysine, and wherein the calix[n]arene-crown-[m]-ether compound is attached to the antibody through an $\epsilon$-amino group of the lysine.

6. The radionuclide delivery system of claim 1 wherein the calix[n]arene-crown-[m]-ether compound is configured to selectively bind radium.

7. The radionuclide delivery system of claim 1 wherein the calix[n]arene-crown-[m]-ether compound is configured to selectively bind $Ra^{2+}$, and comprises calix[4]arene-crown-[6]-ether dicarboxylic acid.

8. A compound comprising:
    a calix[n]arene group, wherein n is an integer greater than 3 and less than 7, the calix[n]arene group comprising an upper rim and a lower rim;
    at least two ionizable groups attached to the lower rim;
    a crown ether attached to the lower rim;
    and a $Ra^{2+}$ ion selectively bond within the crown ether.

9. The compound of claim 8 wherein the crown ether is a crown-[m]-ether, wherein m is an integer greater than 3 and less than 7.

10. The compound of claim 8 wherein the crown ether is a crown-[6]-ether.

11. The compound of claim 8 wherein the crown ether comprises from 1 to 4 aromatic rings.

12. The compound of claim 8 wherein the at least two ionizable groups comprise one or more functional groups selected from the group consisting of carboxylic acid, hydroxamic acid, phosphonic acid, sulfonic acid, diphosphonic acid, and phosphonic acid.

13. The compound of claim 8 further comprising a linking group attached to the upper rim, the linking group being configured to covalently attach the compound to a protein.

14. The compound of claim 8 further comprising a linking group attached to the upper rim, the linking group comprising one or more functional groups selected from the group consisting of amines, aldehydes, esters, alcohols, azides, cyanides, halogens, anhydrides, and acid chlorides.

15. A method of making a radium complexing compound, comprising:
    providing a calix[n]arene compound, wherein n is an integer greater than 3, the calix[n]arene compound comprising n phenolic hydroxyl groups;
    providing a crown ether precursor, the crown ether precursor comprising a pair of tosylated ends;
    reacting the pair of tosylated ends with a pair of the phenolic hydroxyl groups to convert said pair of phenolic hydroxyl groups to ether linkages and to leave remaining phenolic hydroxyl groups which are unreacted with the tosylated ends, the ether linkages connecting the crown ether precursor to the calix[n]arene to form a calix[n]arene-crown-[m]-ether compound, wherein m is an integer greater than 3;

converting at least some of the remaining phenolic hydroxyl groups to esters;

converting the esters to acids, the acids being proximate a crown-[m]-ether portion of the calix[n]arene-crown-[m]-ether compound; and selectively binding a $Ra^{2+}$ ion within the crown-[m]-ether portion of the calix[n]arene-crown-[m]-ether compound.

16. The method of claim 15 wherein n is equal to four.

17. The method of claim 15 wherein the crown ether precursor comprises from 1 to 4 aromatic rings.

18. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming one or more linking groups attached to the upper rim, the linking groups being configured to covalently attach the calix[n]arene-crown-[m]-ether compound to a protein.

19. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming a linking group attached to the upper rim, the linking group comprising a nitrate group; and converting the nitrate group to an amide.

20. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming a linking group attached to the upper rim, the linking group comprising a nitrate group;

converting the nitrate group to an amide; and covalently attaching the amide to a protein.

21. The method of claim 20 wherein the covalently attaching the amide to a protein occurs before selectively binding the $Ra^{2+}$ ion within the crown-[m]-ether portion of the calix[n]arene-crown-[m]-ether compound.

22. The method of claim 20 wherein the covalently attaching the amide to a protein occurs after selectively binding the $Ra^{2+}$ ion within the crown-[m]-ether portion of the calix[n]arene-crown-[m]-ether compound.

23. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming a linking group attached to the upper rim, the linking group comprising an iodo group.

24. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming a linking group attached to the upper rim, the linking group comprising methylene chloride.

25. The method of claim 15 wherein the calix[n]arene-crown-[m]-ether compound comprises a calix[n]arene portion, the calix[n]arene portion having an upper rim and a lower rim, the crown-[m]-ether portion being attached to the lower rim, the method further comprising:

forming a linking group attached to the upper rim, the linking group comprising a compound selected from the group consisting of $CH_2CHO$, $CH_2CH_2OH$, $CH_2CH_2Br$, $CH_2CH_2N_3$, $CH_2CH_2NH_2$, $CH_2CH_2CN$, $CN$, $CH(COOEt)_2$, $CH(NO_2)(COOEt)$, $CH_2Cl$, $CHO$, $NO_2$, and $Br$.

26. A method of extracting a radionuclide, comprising:

providing a sample comprising a radionuclide;

providing a calix[n]arene-crown-[m]-ether compound in contact with the sample, wherein n is an integer greater than 3, and wherein m is an integer greater than 3, the calix[n]arene-crown-[m]-ether compound comprising at least two ionizable groups; and extracting radionuclide from the sample into the calix[n]arene-crown-[m]-ether compound.

27. The method of claim 26 wherein the extracted radionuclide is bound within the calix[n]arene-crown-[m]-ether compound to form a radionuclide complex, the method further comprising:

after the extracting, removing the radionuclide complex from the sample.

28. The method of claim 26 wherein the calix[n]arene-crown-[m]-ether compound is configured to selectively bind $Ra^{2+}$.

29. The method of claim 26 wherein the calix[n]arene-crown-[m]-ether compound is configured to selectively bind $Ra^{2+}$, and comprises calix[4]arene-crown-[6]-ether dicarboxylic acid.

30. A method of delivering a radionuclide to a target location, comprising:

providing a calix[n]arene-crown-[m]-ether compound, wherein n is an integer greater than 3, and wherein m is an integer greater than 3, the calix[n]arene-crown-[m]-ether compound comprising at least two ionizable groups;

providing a radionuclide bound within the calix[n]arene-crown-[m]-ether compound; and providing an antibody attached to the calix[n]arene-crown-[m]-ether compound, the antibody being specific for a material found at the target location.

31. The method of claim 30 wherein the antibody comprises a nitrogen, and wherein the calix[n]arene-crown-[m]-ether compound is attached to the antibody through a covalent bond to the nitrogen.

32. The method of claim 30 wherein the antibody comprises a sulfur, and wherein the calix[n]arene-crown-[m]-ether compound is attached to the antibody through a covalent bond to the sulfur.

33. The method of claim 30 wherein the antibody comprises a phenolic group, and wherein the calix[n]arene-crown-[m]-ether compound is attached to the antibody through a covalent bond to the phenolic group.

34. The method of claim 30 wherein the antibody comprises a lysine, and wherein the calix[n]arene-crown-[m]-ether compound is attached to the antibody through an ϵ-amino group of the lysine.

35. The method of claim 30 wherein the calix[n]arene-crown-[m]-ether compound is configured to selectively bind $Ra^{2+}$, and wherein the radionuclide comprises $Ra^{2+}$.

36. The method of claim 30 wherein the calix[n]arene-crown-[m]-ether compound comprises calix[4]arene-crown-

[6]-ether dicarboxylic acid, and wherein the radionuclide comprises $Ra^{2+}$.

37. The method of claim 30 wherein the target location is a cancer cell.

38. A compound comprising:
   a calix[n]arene group, wherein n is an integer greater than 3 and less than 7, the calix[n]arene group comprising an upper rim and a lower rim;
      at least two dihydroxamic acid ionizable groups attached to the lower rim;
      a crown ether attached to the lower rim;
      and a $Ra^{2+}$ ion held within the crown ether.

39. The compound of claim 38 wherein the crown ether is a crown-[m]-ether, wherein m is an integer greater than 3 and less than 7.

40. The compound of claim 38 wherein the crown ether is a crown-[6]-ether.

41. The compound of claim 38 wherein the crown ether comprises from 1 to 4 aromatic rings.

42. The compound of claim 38 further comprising a linking group attached to the upper rim, the linking group being configured to covalently attach the compound to a protein.

43. The compound of claim 38 further comprising a linking group attached to the upper rim, the linking group comprising one or more functional groups selected from the group consisting of amines, aldehydes, esters, alcohols, azides, cyanides, halogens, anhydrides, and acid chlorides.

44. A method of extracting a radionuclide, comprising:
   providing a sample comprising a radionuclide;
   providing a calix[n]arene-crown-[m]-ether compound in contact with the sample, wherein n is an integer greater than 3, and wherein m is an integer greater than 3, the calix[n]arene-crown-[m]-ether compound comprising at least two dihydroxamic acid ionizable groups; and
   extracting radionuclide from the sample into the calix[n]arene-crown-[m]-ether compound.

45. The method of claim 44 wherein the extracted radionuclide is bound within the calix[n]arene-crown-[m]-ether compound to form a radionuclide complex, the method further comprising:
   after the extracting, removing the radionuclide complex from the sample.

46. The method of claim 44 wherein the calix[n]arene-crown-[m]-ether compound is configured to selectively bind $Ra^{2+}$.

47. The method of claim 44 wherein the calix[n]arene-crown-[m]-ether compound is configured to selectively bind $Ra^{2+}$, and comprises calix[4]arene-crown-[6]-ether dicarboxylic acid.

* * * * *